(12) United States Patent
Shimada et al.

(10) Patent No.: US 8,914,263 B2
(45) Date of Patent: Dec. 16, 2014

(54) INFORMATION PROCESSING APPARATUS, INFORMATION PROCESSING METHOD AND COMPUTER READABLE MEDIUM FOR ASSESSMENT OF EVENT INFLUENCE

(75) Inventors: Yuhei Shimada, Kanagawa (JP); Manabu Ueda, Kanagawa (JP); Yuichi Ueno, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 219 days.

(21) Appl. No.: 13/023,936

(22) Filed: Feb. 9, 2011

(65) Prior Publication Data

US 2012/0046926 A1 Feb. 23, 2012

(30) Foreign Application Priority Data

Aug. 20, 2010 (JP) ................. 2010-184506

(51) Int. Cl.
*G06F 17/00* (2006.01)
*G06F 17/50* (2006.01)
*G06F 19/00* (2011.01)

(52) U.S. Cl.
CPC ........ *G06F 17/5009* (2013.01); *G06F 19/3437* (2013.01); *G06F 19/3493* (2013.01)
USPC ............................................................ 703/6

(58) Field of Classification Search
USPC ............................................................. 703/6
See application file for complete search history.

(56) References Cited

U.S. PATENT DOCUMENTS

2008/0091486 A1* 4/2008 Aoyama et al. .................. 705/7
2008/0130951 A1* 6/2008 Wren et al. .................. 382/103
2008/0215970 A1 9/2008 Tsuji et al.
2008/0301095 A1* 12/2008 Zhu et al. ........................ 707/3
2013/0124227 A1* 5/2013 Ellis .................................. 705/3

FOREIGN PATENT DOCUMENTS

JP 2008-176573 A 7/2008
JP 2009-129388 A 6/2009

OTHER PUBLICATIONS

Christopher L. Barrett, Stephen Eubank, Madhav V. Marathe. An Interaction-Based Approach to Computational Epidemiology. In Dieter Fox, Carla P. Gomes, editors, Proceedings of the Twenty-Third AAAI Conference on Artificial Intelligence, AAAI 2008, Chicago, Illinois, USA, Jul. 13-17, 2008. pp. 1590-1593, AAAI Press, 2008.*

(Continued)

*Primary Examiner* — Omar Fernandez Rivas
*Assistant Examiner* — Robert Brock
(74) *Attorney, Agent, or Firm* — Sughrue Mion, PLLC

(57) ABSTRACT

An information processing apparatus includes an acquiring module, a model generating module and an analyzing module. The acquiring module acquires recording information corresponding to a target event from an event recording information storage device storing the recording information which includes a starting date and time of the target event, an ending date and time of the target event, and a place for an occurrence of the target event. The model generating module sets a date and time before or after a predetermined period since the starting date and time, sets a date and time before or after a predetermined period since the ending date and time, and generates a model including influence information. The analyzing module analyzes an influence of a first event and a second event. The second event is generated in the same place as the place in which the first event occurs.

12 Claims, 42 Drawing Sheets

(56) References Cited

OTHER PUBLICATIONS

Andrea Apolloni et al, A Study of Information Diffusion over a Realistic Social Network Model. In Proceedings of the 2009 International Conference on Computational Science and Engineering—vol. 4 (CSE '09; Aug. 29-13, 2009), vol. 4. IEEE Computer Society, Washington, DC, USA, 675-682.*

Demianyk, B.; Sandison, D.; Libbey, B.; Guderian, R.; McLeod, R.D.; Eskicioglu, M.R.; Friesen, M.R.; Ferens, K.; Mukhi, S.; , "Technologies to generate contact graphs for personal social networks," e-Health Networking Applications and Services (Healthcom), 2010 12th IEEE International Conference on , vol., no., pp. 15-22, Jul. 1-3, 2010.*

Thomas E. Hansen, Juan Pablo Hourcade, Alberto Segre, Chris Hlady, Philip Polgreen, and Chris Wyman, Interactive visualization of hospital contact network data on multi-touch displays. In Proceedings of the 3rd Mexican Workshop on Human Computer Interaction (MexIHC '10; Mar. 2010), Eduardo H. Calvillo Gámez and Victor M. González y González (Eds.).*

Eubank S, Kumar VSA, Marathe M, Srinivasan A, Wang N. Structure of social contact networks and their impact on epidemics. In: In AMS-DIMACS Special Volume on Epidemiology. vol. 70.; (2006).*

Ueda et al., ROBAS: Real Orgranizational Behavior Audit Service, Technical Report No. 17, 1-3 (2007).*

David Keil, Dina Goldin, Indirect Interaction in Environments for Multi-agent Systems Environments for Multi-Agent Systems II, pp. 68-87 (2006).*

S. Eubank and J. Smith, Scalable, efficient epidemiological simulation, In Proceedings of Symposium on Applied Computing, (2002).*

W. Pan, M. Cebrian, W. Dong, T. Kim, and A. Pentland, Modeling dynamical influence in human interaction patterns, (2010) [Online]. Available: Arxiv preprint arXiv:1009.0240.*

JF Allen and G Ferguson. Actions and events in temporal logic, Journal of Logic and Computation, 4(5):53 1-579, 1994, (preprint 58 pages obtained from http://web.mit.edu/larsb/Public/16.412/pset%204/allen94actions.pdf on Jul. 31, 2014).*

Yongmian Zhang; Yifan Zhang; Swears, E.; Larios, N.; Ziheng Wang; Qiang Ji, "Modeling Temporal Interactions with Interval Temporal Bayesian Networks for Complex Activity Recognition," Pattern Analysis and Machine Intelligence, IEEE Transactions on , vol. 35, No. 10, pp. 2468,2483, Oct. 2013, doi: 10.1109/TPAMI.2013.33.*

* cited by examiner

FIG. 8

| STARTING TIME | ENDING TIME | EMPLOYEE ID | DETECTION AREA | INFECTION STATE |
|---|---|---|---|---|
| 2010/3/11 9:00:00 | 2010/3/11 9:30:00 | 001 | LIVING ROOM 201 | INFECTION A |
| 2010/3/11 9:35:00 | 2010/3/11 9:45:00 | 002 | MEETING ROOM B | INFECTION B |
| 2010/3/11 9:45:00 | 2010/3/11 10:00:00 | 005 | LIVING ROOM 201 | GOOD PHYSICAL CONDITION |
| : | : | | | |

FIG. 9

| AREA | AREA TYPE | SIZE [m²] | MEAN TEMPERATURE[°C] | MEAN HUMIDITY [%] |
|---|---|---|---|---|
| LIVING ROOM 201 | LIVING ROOM 1 | 120 | 21 | 28 |
| LIVING ROOM 202 | LIVING ROOM 1 | 180 | 18 | 30 |
| MEETING ROOM B | MEETING ROOM 1 | 30 | 23 | 42 |
| .. | | | | |

FIG. 11

| STARTING TIME 1110 | ENDING TIME 1120 | EMPLOYEE ID 1130 | DETECTION AREA 1140 | INFECTION STATE 1150 | ANALYZING MODEL STARTING TIME 1160 | ANALYZING MODEL ENDING TIME 1170 | INFECTION RISK FUNCTION 1180 |
|---|---|---|---|---|---|---|---|
| 2010/3/11 9:00:00 | 2010/3/11 9:30:00 | 001 | LIVING ROOM 201 | INFECTION A | 2010/3/11 9:00:00 | 2010/3/11 9:45:00 | $\beta_1$ |
| 2010/3/11 9:35:00 | 2010/3/11 9:45:00 | 002 | MEETING ROOM B | INFECTION B | 2010/3/11 9:35:00 | 2010/3/11 9:48:00 | $\beta_3$ |
| 2010/3/11 9:35:00 | 2010/3/11 10:00:00 | 005 | LIVING ROOM 201 | GOOD PHYSICAL CONDITION | 2010/3/11 9:35:00 | 2010/3/11 10:00:00 | $\beta_0$ |
| ... | ... | ... | ... | ... | ... | ... | ... |

| INFECTION RISK FUNCTION 1210 | AREA TYPE 1220 | INFECTION STATE 1230 | RISK DURATION 1240 | INFECTION RISK MAXIMUM VALUE 1250 |
|---|---|---|---|---|
| $\beta_1$ | LIVING ROOM 1 | INFECTION A | 15 | 75 |
| $\beta_2$ | LIVING ROOM 2 | INFECTION A | 15 | 60 |
| $\beta_3$ | MEETING ROOM 1 | INFECTION B | 3 | 25 |
| .. | .. | | | .. |

| INFECTION RISK VALUE | INFECTION RISK DECISION RESULT | RECOMMENDED ACTION |
|---|---|---|
| 1-29 | INFECTION POSSIBILITY: ALMOST LOW | PLEASE TAKE SPECIAL CARE OF PHYSICAL CONDITION |
| 30-59 | INFECTION POSSIBILITY: ALMOST MIDDLE | PLEASE SEE DOCTOR WHEN YOU HAVE FEVER |
| ... | ... | |

*FIG. 18*

INFECTION DISEASE RISK CHECKER (MANAGER EDITION)

Employee ID: 018   Mr./Mrs./Ms.   2010/04/01 15:31

Please select infection risk analyzing item.

■ Analyzing Period:

| From | March 10 | To | March 15 |

■ Analyzing Organization:

○ Full Organization

● Business Department    ○ Research Department

○ General Affairs Department   ○ Development Department

■ Analyzing Area:

○ Full Area    ○ Belonging Floor (6F)

● Belonging Lodgment (Roppongi)

[ Analysis Start ]   [ Reset ]

FIG. 26

| STARTING TIME | ENDING TIME | EMPLOYEE ID | DETECTION AREA |
|---|---|---|---|
| 2010/3/11 9:05:00 | 2010/3/11 9:09:12 | 1230 | LIVING ROOM 201 |
| 2010/3/11 9:07:00 | 2010/3/11 9:12:31 | 2112 | LIVING ROOM 202 |
| .. | .. | | |

| LEAVING STARTING TIME | LEAVING ENDING TIME | DOCUMENT ID | PRINT INDICATOR ID | PRINTER ID |
|---|---|---|---|---|
| 2010/3/11 9:01:00 | 2010/3/11 9:4:45 | a3269 | 2200 | P001 |
| 2010/3/11 9:35:00 | 2010/3/11 9:36:48 | b4856 | 0960 | P003 |
| .. | .. | | | |

FIG. 31

| DISCLOSURE RANGE/ BELONGING | IN-SPECIFIC DEPARTMENT | IN-HOUSE | OUTSIDE COMPANY (NON-COMPETITION) | OUTSIDE COMPANY (COMPETITION) |
|---|---|---|---|---|
| IN-SPECIFIC DEPARTMENT | 0 | 30 | 50 | 100 |
| IN-HOUSE | 0 | 0 | 30 | 60 |
| OUTSIDE COMPANY (NON-COMPETITION) | 0 | 0 | 0 | 40 |
| OUTSIDE COMPANY (COMPETITION) | 0 | 0 | 0 | 0 |

FIG. 33

| STARTING TIME 3310 | ENDING TIME 3320 | EMPLOYEE ID 3330 | DETECTION AREA 3340 | RISK GENERATING TIME 3350 | RISK DISAPPEARING TIME 3360 | RISK EVALUATION MAXIMUM VALUE 3370 |
|---|---|---|---|---|---|---|
| 2010/3/11 9:05:00 | 2010/3/11 9:09:12 | 1230 | LIVING ROOM 201 | 2010/3/11 9:02:00 | 2010/3/11 9:09:48 | 30 |

| 3410 | 3420 | 3430 | 3440 | 3450 | 3460 | 3470 | 3480 | 3490 |
|---|---|---|---|---|---|---|---|---|
| LEAVING STARTING TIME | LEAVING ENDING TIME | DOCUMENT ID | PRINT INDICATOR ID | PRINTER ID | INSTALLATION AREA | RISK GENERATING TIME | RISK DISAPPEARING TIME | RISK EVALUATION MAXIMUM VALUE |
| 2010/3/11 9:01:00 | 2010/3/11 9:04:45 | a3269 | 2200 | P1234 | LIVING ROOM 201 | 2010/3/11 9:00:00 | 2010/3/11 9:04:45 | 1 |

Information leakage risk information (left print)
Employee ID: 2200   Mr./ Mrs./Ms.
Generating time: March 11, 9:04 AM   Document ID: a3269
The document might have been read by employee in other department. Please take care of leaving after printout and improve print action.

INFORMATION PROCESSING APPARATUS, INFORMATION PROCESSING METHOD AND COMPUTER READABLE MEDIUM FOR ASSESSMENT OF EVENT INFLUENCE

CROSS-REFERENCE TO RELATED APPLICATIONS

This application is based upon and claims priority under 35 USC 119 from Japanese Patent Application No. 2010-184506, filed Aug. 20, 2010.

BACKGROUND

Technical Field

The present invention relates to an information processing apparatus, an information processing method and a computer readable medium.

SUMMARY OF THE INVENTION

According to an aspect of the invention, an information processing apparatus includes an acquiring module, a model generating module and an analyzing module. The acquiring module acquires recording information corresponding to a target event from an event recording information storage device storing the recording information which includes a starting date and time of the target event, an ending date and time of the target event, and a place for an occurrence of the target event. The model generating module sets, as a starting date and time of a model, a date and time before or after a predetermined period since the starting date and time of the target event, sets, as an ending date and time of the model, a date and time before or after a predetermined period since the ending date and time of the target event invent, and generates a model including influence information for calculating an influence of the target event. The analyzing module analyzes an influence of a first event and a second event based on an overlap period for which a first period of the first event overlaps a second period of the second event and influence information about a first model of the first event or influence information about a second model of the second event. The first model and the second model are generated by the model generating module. The first period is determined based on starting and ending dates and times of the first model. The second period is determined based on starting and ending dates and times of the second model. The second event is generated in the same place as the place in which the first event occurs.

BRIEF DESCRIPTION OF THE DRAWINGS

Exemplary embodiments of the invention will be described in detail based on the following figures, wherein:

FIG. 8 is an explanatory diagram showing an example of a data structure of an action log data table;

FIG. 9 is an explanatory diagram showing an example of a data structure of an area data table;

FIG. 11 is an explanatory diagram showing an example of a data structure of an analyzing model data table;

FIG. 12 is an explanatory diagram showing an example of a data structure of an infection risk function data table;

FIG. 14 is an explanatory diagram showing an example of a data structure of an infection risk deciding table;

FIG. 18 is an explanatory diagram showing an example of an analyzing condition setting screen;

FIG. 26 is an explanatory diagram showing an example of a data structure of an action log table;

FIG. 29 is an explanatory diagram showing an example of a data structure of a print log table;

FIG. 31 is an explanatory diagram showing an example of a data structure of a risk evaluation maximum value deciding table;

FIG. 33 is an explanatory diagram showing an example of a data structure of an action log information leakage risk analyzing model table;

FIG. 34 is an explanatory diagram showing an example of a data structure of an information leakage risk analyzing model table of an apparatus operating log;

FIG. 35 is an explanatory diagram showing an example of an analysis result notifying screen;

DETAILED DESCRIPTION

With reference to the drawings, description will be given to examples of various exemplary embodiments which are suitable for implementing the invention.

Six exemplary embodiments will be described. First three of them, that is, (1-A)th, (1-B)th and (1-C)th exemplary embodiments mainly illustrate the case in which an analyzing target is an infection risk of a virus of a flu, and the other three of them, that is, (2-A)th, (2-B)th and (2-C)th exemplary embodiments mainly illustrate the case in which an analyzing target is a risk of an information leakage caused by stealing a glance at an output result obtained by an image output device (for example, a printer or a display).

Figure 1:
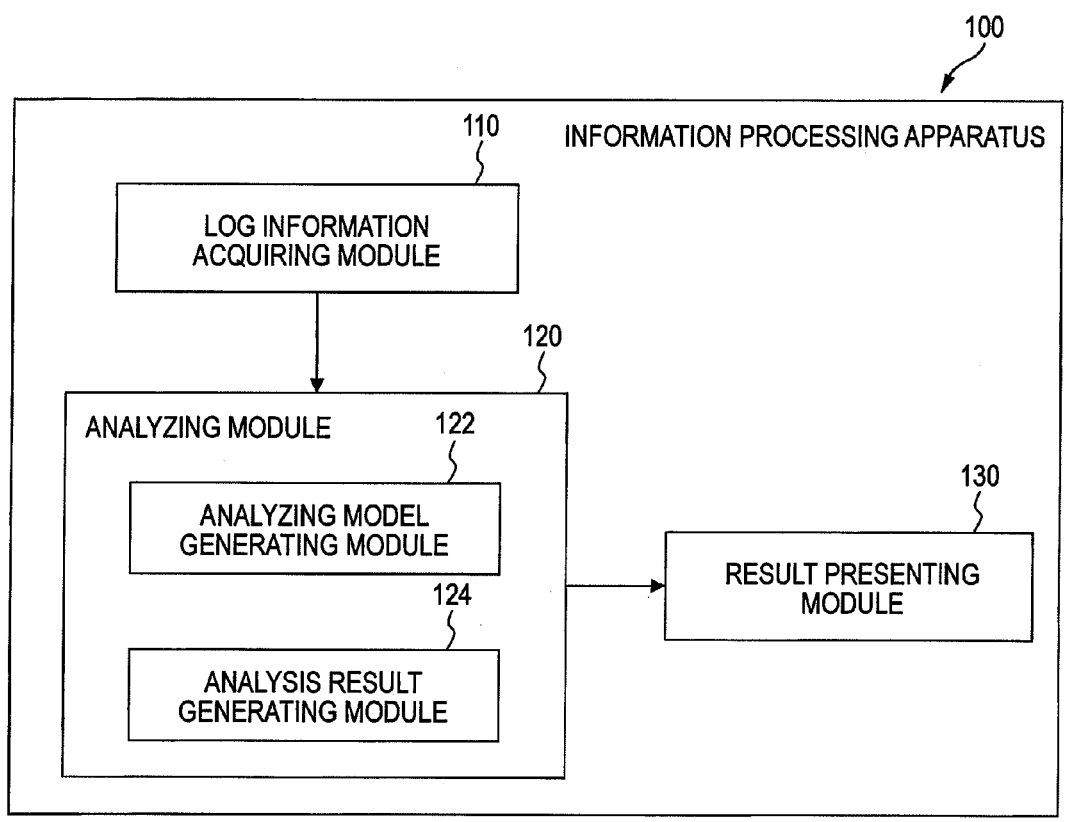
FIG. 1 is a diagram showing a conceptual module structure according to an example of a structure in accordance with a (1-A)th exemplary embodiment.

FIG. 1 is a diagram showing a conceptual module structure according to an example of a structure in accordance with the (1-A)th exemplary embodiment.

A module indicates a component such as software (a computer program) or hardware which may be separated generally and logically. Accordingly, the module according to the exemplary embodiment indicates a module in a hardware structure in addition to a module in a computer program. Therefore, the exemplary embodiment also applies to description of a computer program caused to function as the modules (a program for causing a computer to execute respective procedures, a program for causing the computer to function as respective means or a program for causing the computer to implement respective functions), a system and a method. For convenience of the description, "store", "stored" and equivalent words thereto are used. In the case in which the exemplary embodiment relates to a computer program, however, the words imply that the computer program is stored in a storage device or is controlled to be stored in the storage device. Although the module may carry out a one-to-one correspondence to the function, moreover, a single module may be constituted by a single program or a plurality of modules may be constituted by a single program, and to the contrary, a single module may be constituted by a plurality of programs in mounting. Furthermore, the modules may be executed by a single computer or a single module may be executed by a plurality of computers in a distributing or parallel environment. One of the modules may include the other modules. Furthermore, a "connection" is used also in the case of a logical connection (a transfer and receipt of data, an instruction or a reference relationship between data) in addition to a physical connection. "Predetermined" implies a determination before a target processing and is used to imply that a determination is carried out depending on a situation and state at that time or a situation and state brought till that time before a processing according to the exemplary embodiment is started, and furthermore, before a target processing after the processing according to the exemplary embodiment is started.

Moreover, a system or a device is constituted by connecting computers, hardware or devices through communicating means such as a network (including a one-to-one corresponding communicating connection), and furthermore, is implemented by a single computer, hardware or device. The "device" and the "system" are used as synonymous words with each other. As a matter of course, the "system" does not include a social and simple "mechanism" (a social system) which is an artificial arrangement.

For every processing to be executed through each module or each of a plurality of processings to be executed in the module, moreover, target information is read from a storage device, the processing is executed and a result of the processing is then written to the storage device. In some cases, accordingly, there will be omitted description of the read from the storage device before the processing and the write to the storage device after the processing. The storage device may include a hard disk, an RAM (Random Access Memory), an external storage medium, a storage device through a communication line and a register in a CPU (Central Processing Unit).

An information processing apparatus 100 according to the (1-A)th exemplary embodiment has a log information acquiring module 110, an analyzing module 120 and a result presenting module 130 as shown in an example of FIG. 1.

The log information acquiring module 110 is connected to the analyzing module 120. The log information acquiring module 110 acquires recording information about a target event from an event recording information storage device which stores recording information (hereinafter referred to as log information) about an event including at least a starting date and time of an event, an ending date and time of the event and a place for an occurrence of the event. For example, the log information acquiring module 110 acquires log information about a position or a state of a person or a thing at a certain time. Attribute information about a person or a thing may be acquired together with the log information.

If an analyzing target is an infection risk of a virus of a flu, a certain person entering/leaving a certain room corresponds to an event. In this case, the starting date and time of the event corresponds to a date and time that the person enters the room (the date and time may include a year, a month, a minute, a second and the like in addition to one of a date and a time or their combination if a time may be uniquely specified according to the exemplary embodiment, and so forth). A date and time that the person leaves the room corresponds to the ending date and time of the event. The room corresponds to the place for the occurrence of the event.

The event recording information storage device may be provided in the information processing apparatus 100 or may be provided on an outside of the information processing apparatus 100 and may be connected through a communication line if access may be given from the log information acquiring module 110.

The analyzing module 120 has an analyzing model generating module 122 and an analysis result generating module 124. The analyzing module 120 is connected to the log information acquiring module 110 and the result presenting module 130. The analyzing module 120 carries out an analysis by using log information.

The analyzing model generating module 122 sets, as a starting date and time of a model, a date and time before or after a predetermined period since a starting date and time in recording information about an event which is acquired by the log information acquiring module 110 (a date and time before the predetermined period will be mainly illustrated), sets, as an ending date and time of the model, a date and time before or after a predetermined period since an ending date and time in the recording information about the event (a date and time after the predetermined period will be mainly illustrated), and generates a model including at least influence information for calculating an influence of the event. The analyzing model generating module 122 generates an analyzing model obtained by adding analyzing model information meeting an analyzing object to the acquired log information.

The analysis result generating module 124 analyses an influence of a first event and a second event based on a period for which a period determined by a starting date and time and an ending date and time of a model of the first event which is generated by the analyzing model generating module 122 overlaps with a period determined by a starting date and time and an ending date and time of a model of the second event which is generated by the analyzing model generating module 122 and influence information about the model of the first event or influence information about the model of the second event. The analysis result generating module 124 generates an analysis result meeting an analyzing object from the analyzing model generated by the analyzing model generating module 122.

The second event is generated in the same place as the place in which the first event occurs.

The result presenting module 130 is connected to the analyzing module 120. The result presenting module 130 outputs an analysis result obtained by the analyzing result generating module 124. Outputting includes a presentation to a user, more specifically, a display of the analysis result on a display device such as a display, an output of the analysis result in a voice through a voice output device such as a speaker, and furthermore, a print of the analysis result through a printing device such as a printer, a transmission of an image of the analysis result through an image transmitting device such as a FAX, a write of the analysis result to a storage device and a transfer to another image processing apparatus, for example.

Figure 2:
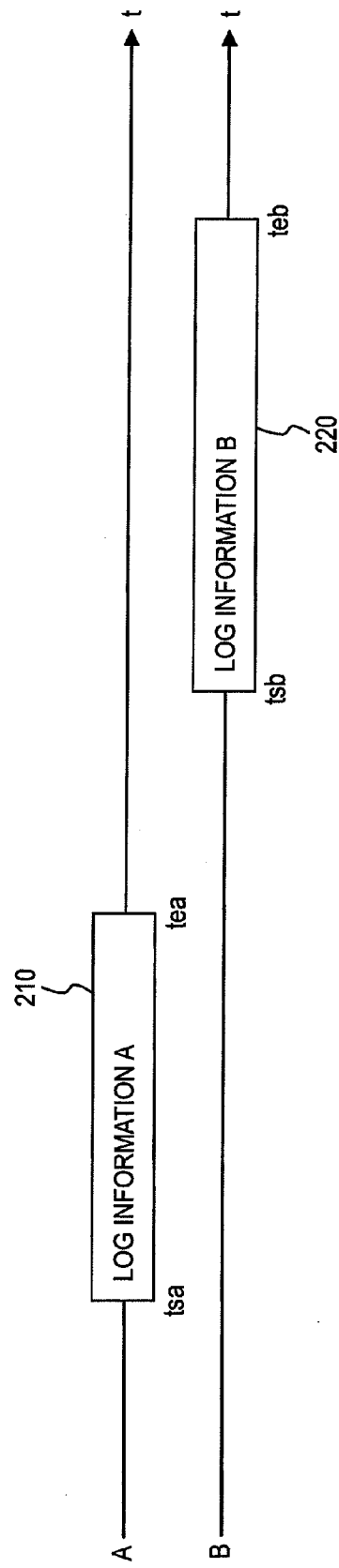
FIG. 2 is an explanatory diagram showing an example of log information.

FIG. 2 is an explanatory diagram showing an example of the log information. This shows the log information in the case in which a certain situation is generated for a target A or B to be a person or a thing. For example, log information A210 about an event that the target person A stays in a reception room includes reception room information indicative of a time (tsa) that the target person A enters the room, that is, a starting date and time of an event, a time (tea) that the target person A leaves the room, that is, an ending date and time of the event, and the reception room to be a place in which the event occurs. Log information B220 in the case in which the target person A leaves the room and the target person B then enters and leaves the same reception room also includes reception room information indicative of a time (tsb) that the target person B enters the room, that is, a starting date and time of an event, a time (teb) that the target person B leaves the room, that is, an ending date and time of the event, and a reception room to be a place in which the event occurs. In this case, a processing is executed on the assumption that the target person A does not meet the target person B in the reception room and the target person B is generally prevented from being influenced by the fact that the target person A stays in the reception room.

The log information acquiring module 110 acquires the log information.

Figure 3:
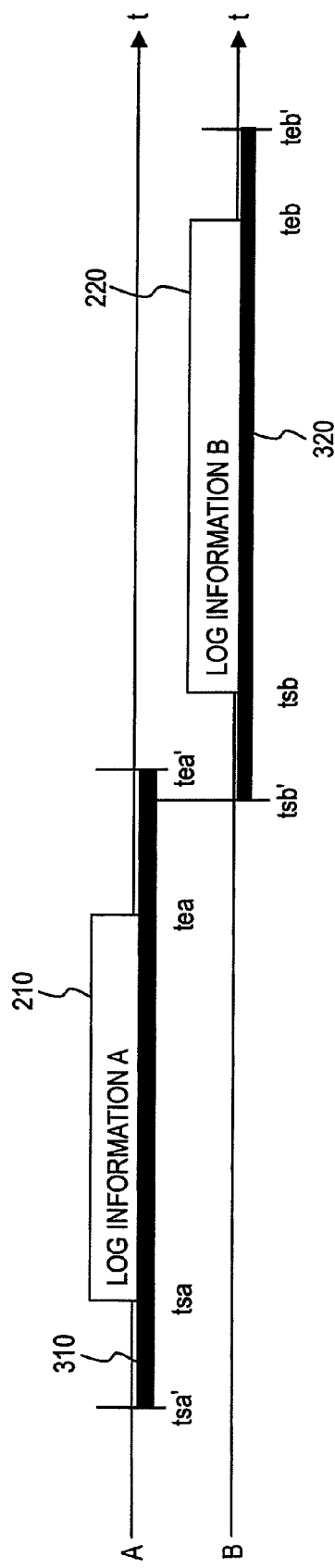
FIG. 3 is an explanatory diagram showing an example of an analyzing model in which analyzing model information is added to the log information.

FIG. 3 is an explanatory diagram showing an example of an analyzing model in which analyzing model information is added to the log information. This shows that the analyzing model information corresponding to analyzing items are added to the log information A and the log information B, respectively. Examples of the analyzing item include an infection risk of a virus of a flu.

Analyzing model information A310 includes analyzing model attached information to be influence information for calculating a time tsa' before a predetermined period since the time tsa, a time tea' after a predetermined period since the time tea, and an influence of an event in addition to the log information A210.

Analyzing model information B320 includes analyzing model attached information to be influence information for calculating a time tsb' before a predetermined period since the time tsb, a time tea' after a predetermined period since the time teb, and an influence of an event in addition to the log information B220.

Referring to the analyzing model attached information, an analysis result is changed with a time. For example, a function indicative of a change in a concentration of a virus corresponds to the analyzing model attached information. More specifically, a damping function determined by a place or an infection disease type corresponds to the analyzing model attached information. In an example of FIG. 3, a period from the time tsa to the time tsa' indicates a possibility that an infection from the target person A to the target person B might be carried out even if the target person B does not directly meet the target person A in the case in which the target person A is infected with a certain virus.

The analyzing model generating module 122 generates the analyzing model information A310 and the analyzing model information B320.

Figure 4:
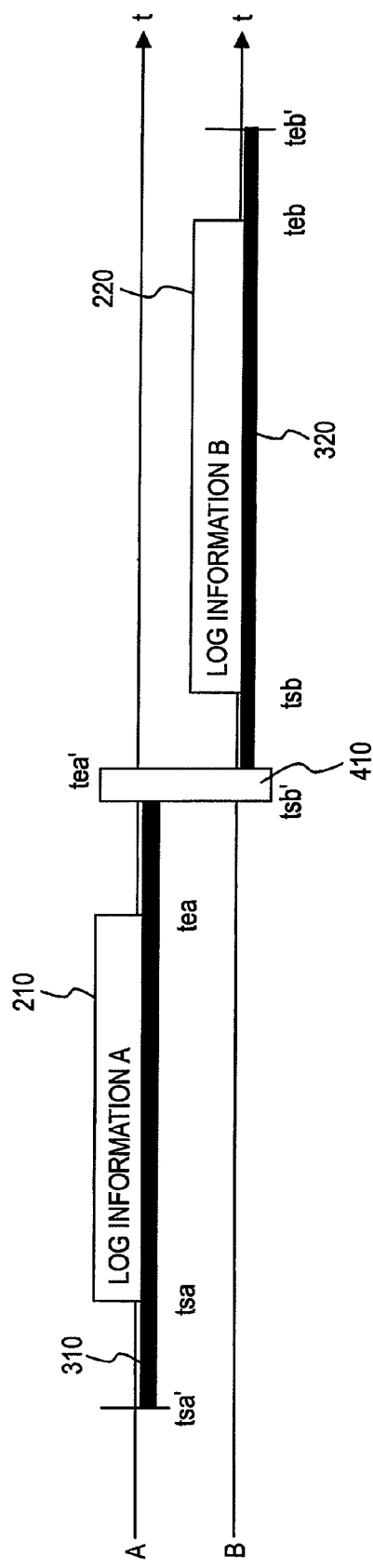
FIG. 4 is an explanatory diagram showing an example of an overlapping period for the analyzing model.

FIG. 4 is an explanatory diagram showing an example of an overlapping period of an analyzing model. This shows that there is an analyzing model overlapping period 410 to be a period for which the analyzing model information A310 and the analyzing model information B320 overlap with each other. This indicates a state of a so-called medical incident (no accident such as an infection on the brink of an occurrence). Consequently, the analysis result generating module 124 analyzes an influence of an event in which the target person A stays in a reception room and an event in which the target person B stays in the same reception room.

More detailed description will be given.

The analyzing model generating module 122 applies an analyzing model generating function F to Equation (1) indicative of each element of a log information set X to generate Equation (2).

$$x = <ts, te, \alpha1, \alpha2, \ldots, \alpha n> \quad \text{Equation (1)}$$

$$F(x) = <ts, te, \alpha1, \alpha2, \ldots, \alpha n, ts', te', \beta1(t), \ldots \beta m(t)> \quad \text{Equation (2)}$$

As a result, the analyzing model generating module 122 outputs Equation (3) to the analysis result generating module 124.

$$U = \{F(x) | x \in X\} \quad \text{Equation (3)}$$

ts represents a starting time, te represents an ending time, $\alpha i$ represents log attached information such as a place or an employee ID, ts' represents an analyzing model starting time, te' represents an analyzing model ending time, and βi(t) represents analyzing model attached information.

Next, the analysis result generating module 124 calculates Equation (4) to be an analysis result for each element ui of a set U of an analyzing model generated by the analyzing model generating module 122.

$$\{<ui,uj,G(ui,uj)>|ui \in U, uj \in U, ui \neq uj\}$$ Equation (4)

Figure 32:
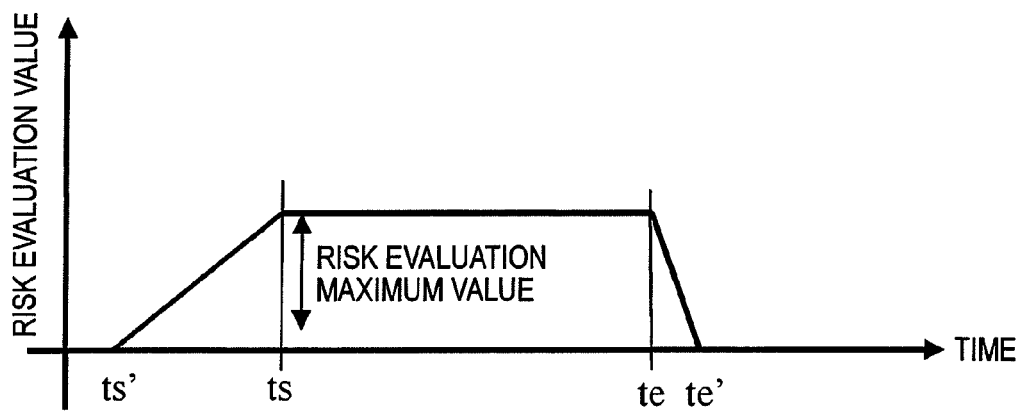
FIG. 32 is an explanatory chart showing an example of a change in a risk evaluation value.

G(ui, uj) will be described below by using an example of FIG. 13 or 32.

Figure 5:
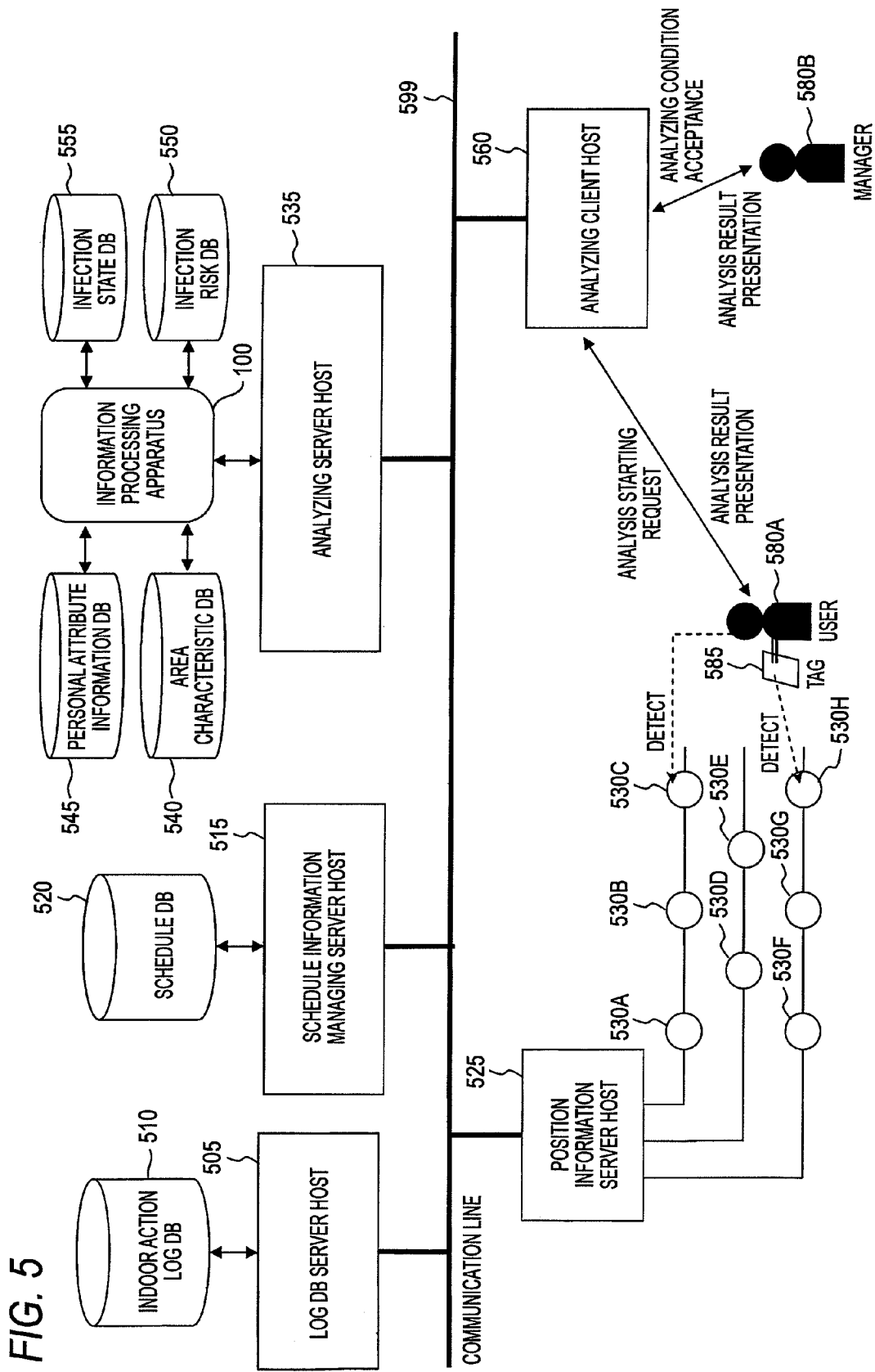
FIG. 5 is an explanatory diagram showing an example of a system structure in the case in which the (1-A)th exemplary embodiment is materialized.

FIG. 5 is an explanatory diagram showing an example of a system structure in the case in which the (1-A)th exemplary embodiment is materialized.

The example of the system structure applies to the case in which the (1-B)th exemplary embodiment (an information processing apparatus) and the (1-C)th exemplary embodiment (an information processing apparatus 2000) are materialized in addition to the (1-A)th exemplary embodiment (the information processing apparatus 100).

A log DB server host 505, a schedule information managing server host 515, a position information server host 525, an analyzing server host 535 and an analyzing client host 560 are connected through a communication line 599, respectively. The log DB server host 505 and an indoor action log DB 510 are connected to each other. The schedule information managing server host 515 and a schedule DB 520 are connected to each other. The analyzing server host 535 is connected to the information processing apparatus 100. The information processing apparatus 100 is connected to the analyzing server host 535, an area characteristic DB 540, a personal attribute information DB 545, an infection risk DB 550 and an infection state DB 555. The position information server host 525 is connected to position sensors 530A to 530H.

A user 580A holds a tag 585 (for example, active RFID (Radio Frequency IDentification)). The tag 585 is detected by the position sensors 530A to 530H. Each of the position sensors reads user information which indicates a user and is stored in the tag 585 (for example, an employee ID (IDentification)), and stores the user information in the position information server host 525 together with a detecting date and time and a position of the position sensor itself. For example, in the case in which the position sensor is attached to each room, action log data indicative of anyone, any time and any room are collected into the position information server host 525. The action log data thus collected are transferred to the log DB server host 505 and an action log data table 800 illustrated in FIG. 8 is stored in the indoor action log DB 510.

Moreover, the user 580A sets a schedule by using the schedule information managing server host 515. Information about the schedule setting is stored in the schedule DB 520. The schedule information managing server host 515 may acquire the information about the schedule setting from a scheduler program in an information processing apparatus such as a PC of each person.

The analyzing client host 560 accepts an operating instruction to be an analysis starting request given by the user 580A and transfers the operating instruction to the analyzing server host 535, and causes the information processing apparatus 100 to analyze an infection risk of a virus of a flu, for example. The information processing apparatus 100 uses data in the personal attribute information DB 545, the area characteristic DB 540, the infection state DB 555 and the infection risk DB 550 or data in the indoor action log DB 510 and the schedule DB 520 to carry out an analysis, presents an analysis result to the analyzing client host 560 through the analyzing server host 535, and informs the user 580A of the analysis result.

Moreover, the analyzing client host 560 accepts an analyzing condition given by a user 580B and transfers the analyzing condition to the analyzing server host 535, and causes the information processing apparatus 100 to analyze the infection risk of the virus of the flu on the analyzing condition, for example. The information processing apparatus 100 uses the data in the personal attribute information DB 545, the area characteristic DB 540, the infection state DB 555 and the infection risk DB 550 or the data in the indoor action log DB 510 and the schedule DB 520 to carry out an analysis depending on the analyzing condition, presents an analysis result to the analyzing client host 560 through the analyzing server host 535, and informs the user 580B of the analysis result.

Figure 6:
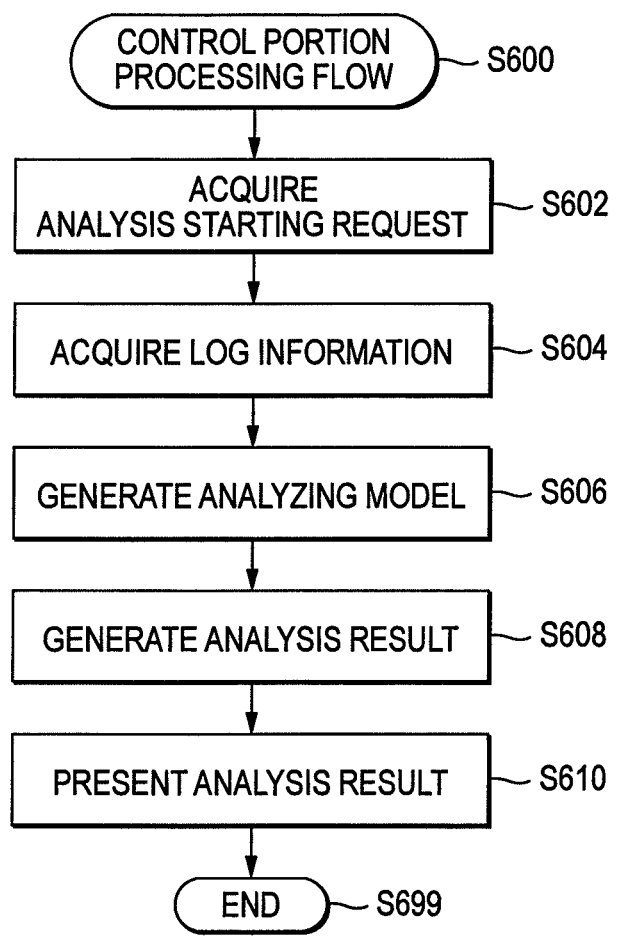
FIG. 6 is a flowchart showing an example of a processing according to the (1-A)th exemplary embodiment.

FIG. 6 is a flowchart showing an example of a processing according to the (1-A)th exemplary embodiment.

Figure 7:
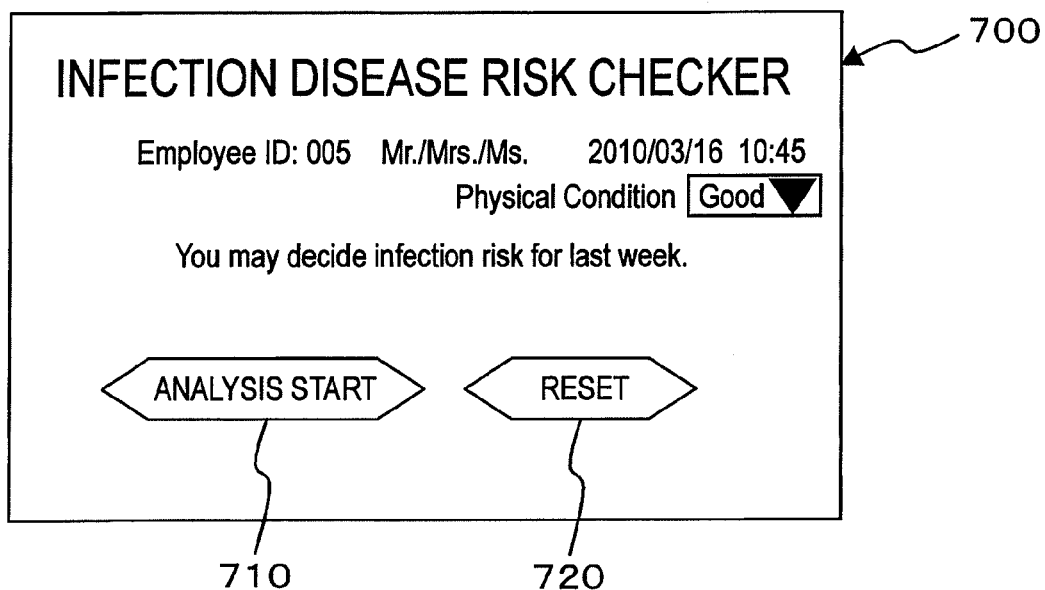
FIG. 7 is an explanatory diagram showing an example of an infection disease risk check screen.

At Step S602, the information processing apparatus 100 acquires an operating instruction to be an analysis starting request through an operation of a mouse, a keyboard or a touch panel by a user. For example, an infection disease risk check screen 700 illustrated in FIG. 7 is presented to the information processing apparatus which may be operated by the user. The infection disease risk check screen 700 has an analysis starting button 710 and a reset button 720. The analysis starting button 710 is selected so that the processing is started. Moreover, user information indicative of the user (an employee ID (IDentification) in the example of FIG. 7) is also acquired. In order to acquire the user information, it is preferable to utilize the user information at time of log-in to the information processing apparatus. Furthermore, it is also possible to acquire a physical condition of the user.

The user is referred to as an employee, a person or a manager depending on a context.

At Step S604, the log information acquiring module 110 acquires log information from the indoor action log DB 510. The indoor action log. DB 510 stores log data to be a record of a past action of each person, particularly, log data catching an actual result of an indoor action. For example, the action log data table 800 illustrated in FIG. 8 is stored. FIG. 8 is an explanatory diagram showing an example of a data structure of the action log data table 800. The action log data table 800 has a starting time column 810, an ending time column 820, an employee ID column 830, a detection area column 840, and an infection state column 850. The starting time column 810 stores a date and time that a user of the employee ID column 830 enters a room of the detection area column 840. The ending time column 820 stores a date and time that the user of the employee ID column 830 leaves the room of the detection area column 840. The employee ID column 830 stores user information indicative of a target user. For example, an employee ID is stored. The detection area column 840 stores area information indicative of an area (a place) in which the user (accurately, the tag 585 held by the user) is detected. For example, a name of a meeting room is stored. The infection state column 850 stores an infection state of the user of the employee ID column 830 between the starting time column 810 and the ending time column 820. The infection state is stored as personal attribute information in the personal attribute information DB 545 and is acquired therefrom. The infection state is based on log data such as a self-report, a result of a medical examination or a detection result obtained by a thermosensor, or log data of a cough sensor. Moreover, the infection state may be a virus name, a state of a symptom or their combination (for example, an incipient state of a tuberculosis or a terminal stage of a flu). Furthermore, the action log data table 800 may include a past infection history, presence of a mask wear and a cough detection result as log information.

In addition, a characteristic to be an attribute of an area in the detection area column 840 of the action log data table 800 may be fetched from the area characteristic DB 540. The area characteristic DB 540 stores an area data table 900, for example. FIG. 9 is an explanatory diagram showing an example of a data structure of the area data table 900. The area data table 900 has an area column 910, an area type column 920, a size column 930, a mean temperature column 940, and a mean humidity column 950. The area column 910 stores area information indicative of an area. For example, a name of a meeting room is stored. The area type column 920 stores a type of the area. For example, a living room or a meeting room is stored. The size column 930 stores a size of the area. The mean temperature column 940 stores a mean temperature in the area. The mean humidity column 950 stores a humidity in the area. The mean temperature column 940 and the mean humidity column 950 may use data on a temperature/humidity measured actually. Moreover, the area data table 900 may include a final ventilation time as a characteristic of the area.

It is also possible to retrieve the area column 910 of the area data table 900 corresponding to the area of the detection area column 840 which is set to be a target, thereby acquiring a characteristic of the area (the area type column 920, the size column 930, the mean temperature column 940 or the mean humidity column 950).

Figure 10:
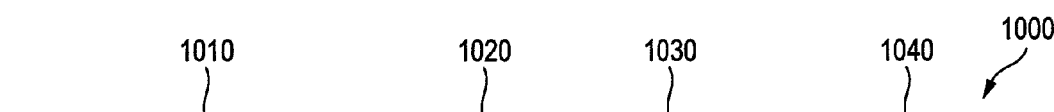
FIG. 10 is an explanatory diagram showing an example of a data structure of an infection state data table.

Moreover, it is also possible to fetch an attribute of an infection state in the infection state column 850 of the action log data table 800 from the infection state DB 555 based on the infection state. The infection state DB 555 stores an infection state data table 1000, for example. FIG. 10 is an explanatory diagram showing an example of a data structure of the infection state data table 1000. The infection state data table 1000 has an infection state column 1010, a toxicity column 1020, an infectivity column 1030 and an infection route column 1040. The infection state column 1010 stores an infection state. The toxicity column 1020 stores a toxicity in the infection state. The infectivity column 1030 stores an infectivity in the infection state. The infection route column 1040 stores an infection route in the infection state. The toxicity column 1020 and the infectivity column 1030 influence a maximum value of an infection value. The infection route column 1040 has an air infection, a droplet infection and a contagion, and is related to a duration of the infection value.

It is also possible to retrieve the infection state column 1010 of the infection state data table 1000 corresponding to the infection state of the infection state column 850 which is set to be a target, thereby acquiring an attribute of the infection state (the toxicity column 1020, the infectivity column 1030 or the infection route column 1040).

At Step S606, the analyzing model generating module 122 generates an analyzing model. The analyzing model is generated based on the log information (the action log data table 800) acquired at the Step S604, the area data (the area data table 900) and the infection state data (the infection state data table 1000). For example, the analyzing model to be generated includes an analyzing model data table 1100. FIG. 11 is an explanatory diagram showing an example of a data structure of the analyzing model data table 1100. The analyzing model data table 1100 has a starting time column 1110, an ending time column 1120, an employee ID column 1130, a detection area column 1140, an infection state column 1150, an analyzing model starting time column 1160, an analyzing model ending time column 1170, and an infection risk function column 1180. The starting time column 1110 to the infection state column 1150 correspond to the starting time column 810 to the infection state column 850 in the action log data table 800, and store a starting time, an ending time, an employee ID, a detection area and an infection state which are acquired respectively. The analyzing model starting time column 1160 to the infection risk function column 1180 are added as the analyzing model. The analyzing model starting time column 1160 stores a date and time before a predetermined period (in this case, zero second) since a starting time stored in the starting time column 1110. The analyzing model ending time column 1170 stores a date and time after a predetermined period since an ending time stored in the ending time column 1120. The infection risk function column 1180 stores an infection risk function to be influence information for calculating an influence of an event.

Description will be given to a generation of data in the analyzing model starting time column 1160 to the infection risk function column 1180. There is applied an infection risk function corresponding to a combination of the detection area characteristic (the size, temperature or humidity of the area data table 900) and the infection state (the infectivity, toxicity or infection route of the infection state data table 1000) based on the analyzing model generating function F.

First of all, description will be given to an infection risk function data table 1200 to be utilized for generating an analyzing model. The infection risk DB 550 stores the infection risk function data table 1200, for example. FIG. 12 is an explanatory diagram showing an example of a data structure of the infection risk function data table 1200. The infection risk function data table 1200 has an infection risk function column 1210, an area type column 1220, an infection state column 1230, a risk duration column 1240, and an infection risk maximum value column 1250. The infection risk function column 1210 stores an infection risk function for obtaining an infection risk value. The area type column 1220 stores an area type applying the infection risk function. The infection state column 1230 stores an infection state applying the infection risk function. In other words, in the case of a coincidence with the conditions of the infection risk function column 1210 and the area type column 1220, the infection risk function is applied. The risk duration column 1240 stores a duration of the infection risk. A value of the risk duration column 1240 is set based on a dropping speed of a droplet nucleus of the air infection or a dropping speed of a droplet particle of the droplet infection. The infection risk maximum value column 1250 stores a maximum value in the risk of the infection.

At Step S608, the analysis result generating module 124 generates an analysis result related to a user indicated by the user information acquired at the Step S602. For example, it is found that an employee having an employee ID of 001 stays in a living room 201 at 9:00:00 to 9:30:00 and an employee having an employee ID of 005 stays in the living room 201 at 9:35:00 to 10:00:00 based on the starting time column 1110, the ending time column 1120, the employee ID column 1130 and the detection area column 1140. It is found that the employee having the employee ID of 001 is brought into an infection state of an infection A based on the infection state column 1150. Moreover, the living room 201 has an area type of a living room 1 based on the area type column 920 of the area data table 900. An infection risk function which is suitable for the area type of the living room 1 and the infection state of the infection A is $\beta_1$ based on the infection risk function data table 1200. Thus, the infection risk function to be stored in the infection risk function column 1180 is acquired. Referring to the infection risk function of $\beta_1$, a risk duration of 15 minutes is obtained from the risk duration column 1240. Accordingly, the analyzing model ending time to be stored in the analyzing model ending time column 1170 is equal to a time (09:45:00) obtained by adding 15 minutes to the ending time column 1120. The infection risk maximum value is 75 based on the infection risk maximum value column 1250. Therefore, an infection risk value in the living room 201 between the employee ID of 001 and the employee ID of 005 is expressed in a graph shown in the example of FIG. 13. An infection risk value to be a risk evaluation value is 75 since 09:30:00 that the employee ID of 001 enters the room, is started to be reduced at 09:30:00 that the employee ID of 001 leaves the room, and is decreased down to 15 minutes to be a risk duration. It is indicated that the risk evaluation value is 50 at 09:35:00 that the employee ID of 005 enters the room.

Figure 13:
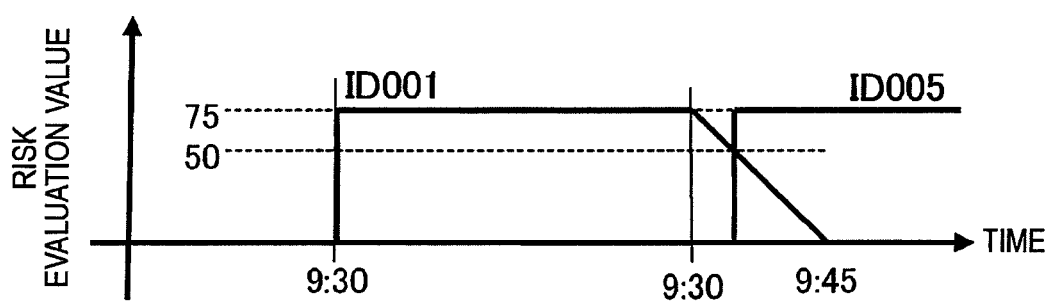
FIG. 13 is an explanatory chart showing an example of a change in a risk evaluation value.

A value having the highest infection risk for a period in which the analyzing models of the employee ID of 001 (an infected person) and the employee ID of 005 (a good physical condition) overlap with each other on a time base is set to be an infection risk value (50 in the example of FIG. 13). The infection risk value may be calculated by setting, as an integral range, a period for which the analyzing models overlap with each other on the time base or may be a sum of the infection risk values at respective times in the case in which a function is discretely defined.

As an analysis based on the infection risk value, a result of a decision of the infection risk or a recommended action is acquired from an infection risk deciding table 1400 in the infection risk DB 550. FIG. 14 is an explanatory diagram showing an example of a data structure of the infection risk deciding table 1400. The infection risk deciding table 1400 has an infection risk value column 1410, an infection risk decision result column 1420, and a recommended action column 1430. The infection risk value column 1410 stores a range of the infection risk value. The infection risk decision result column 1420 stores infection risk decision result information indicative of a possibility of the infection within the range of the infection risk value. The recommended action column 1430 stores recommended action information within the range of the infection risk value. The analysis result generating module 124 acquires a row within the range of the infection risk value to which the infection risk value corresponds, and acquires information in the infection risk decision result column 1420 and the recommended action column 1430 in that row.

Figure 15:
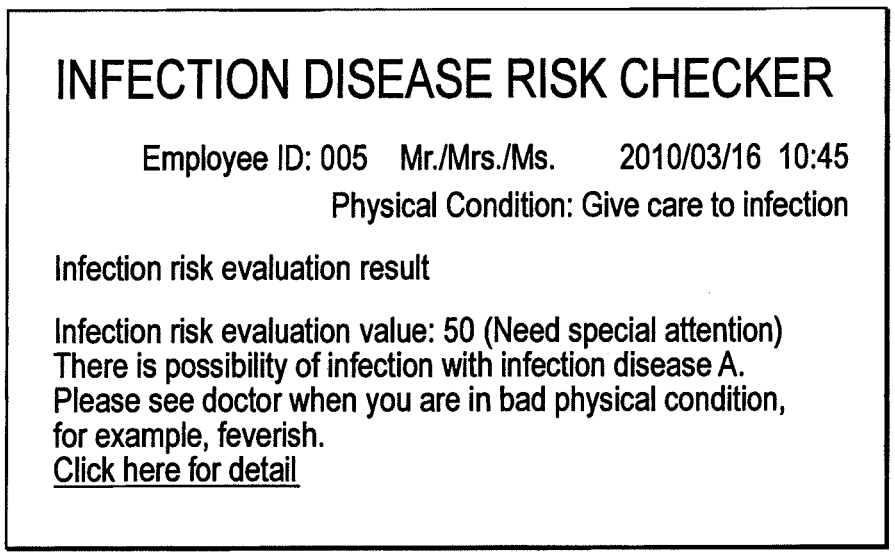
FIG. 15 is an explanatory diagram showing an example of an infection disease risk evaluation result screen.

At Step S610, the result presenting module 130 presents the analysis result at the Step S608. For example, the analysis result is presented to a display device of the information processing apparatus which may be operated by a user as in an infection disease risk evaluation result screen 1500 illustrated in FIG. 15.

In order to generate an analysis result related to a user indicated by the user information acquired at the Step S602, in the example of the processing, the log information acquiring module 110 fetches all of the action log data, the analyzing model generating module 122 generates all of the analyzing models, and the analysis result generating module 124 acquires a user B for whom a period from the starting time to the ending time of the analyzing model of the user A to be the target overlaps with a period from the starting time to the ending time of the analyzing model in the same area as the user A.

However, the log information acquiring module 110 may retrieve, from the employee ID column 830, the employee ID corresponding to the user information acquired at the Step S602, may acquire the log information (the starting time column 810, the ending time column 820, the employee ID column 830, the detection area column 840 and the infection state column 850), may fetch a room in which the user A stays from the detection area column 840, and may fetch log information about the user B who stays in the same room. In other words, the log information acquiring module 110 may acquire only action log data on the user A indicated by the user information acquired at the Step S602 and the user B who might be related to the user A. The analyzing model generating module 122 may generate their analyzing models and the analysis result generating module 124 may acquire the user B for whom the period from the starting time to the ending time of the analyzing model of the user A to be the target overlaps with the period from the starting time to the ending time of the analyzing model.

Figure 16:
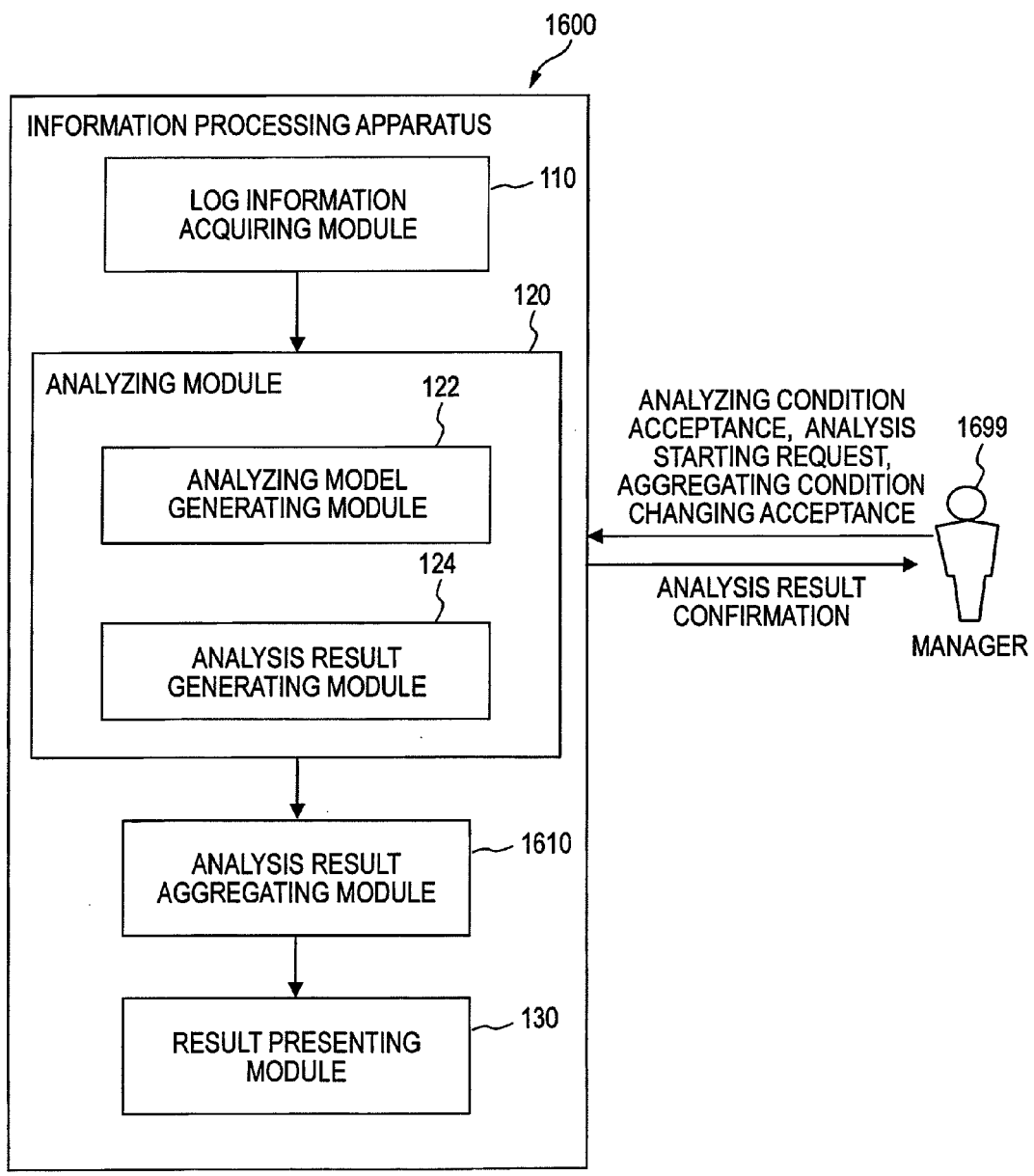
FIG. 16 is an explanatory diagram showing a conceptual module structure according to an example of a structure in accordance with a (1-B)th exemplary embodiment.

FIG. 16 is a diagram showing a conceptual module structure according to an example of a structure in accordance with the (1-B)th exemplary embodiment. An information processing apparatus 1600 has a log information acquiring module 110, an analyzing module 120, an analysis result aggregating module 1610 and a result presenting module 130. The same types of portions as those in the (1-A)th exemplary embodiment have the same reference numerals and repetitive description will be omitted (and set forth).

The user according to the (1-A)th exemplary embodiment is a general user and the analysis result of the infection risk of the user himself (herself) is presented. A user according to the (1-B)th exemplary embodiment is a manager, and an analysis result of an infection risk of a specific person is not presented but analysis results of infection risks of people belonging to a certain organization are presented, for example.

For this purpose, the information processing apparatus 1600 acquires an analyzing condition, an analysis starting request or an aggregating condition change which is an operating instruction through an operation of a mouse, a keyboard or a touch panel by a manager 1699.

The analysis result aggregating module 1610 is connected to the analyzing module 120 and the result presenting module 130, and totalizes an analysis result obtained by an analysis result generating module 124 based on the operating instruction of the manager 1699. For example, it is also possible to totalize the number of people for each extent of a possibility of an infection that is a decision result of an infection risk for a person which is coincident with the analyzing condition.

The result presenting module 130 is connected to the analysis result aggregating module 1610 and a totalization result obtained by the analysis result aggregating module 1610 is presented to the manager 1699.

Figure 17:
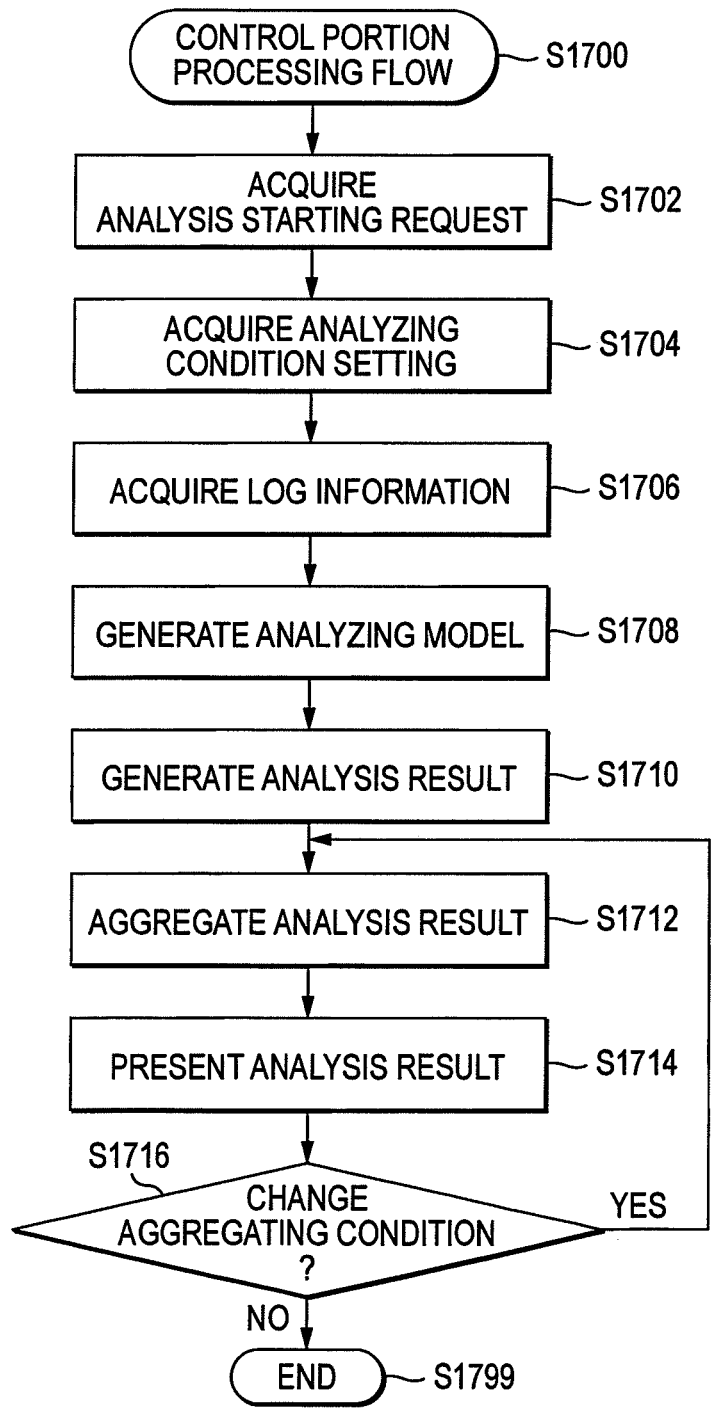
FIG. 17 is a flowchart showing an example of a processing according to the (1-B)th exemplary embodiment.

FIG. 17 is a flowchart showing an example of a processing according to the (1-B)th exemplary embodiment. In the case of the same processing as that in the flowchart showing the example of the processing according to the (1-A)th exemplary embodiment illustrated in FIG. 6, the steps illustrated in the example of FIG. 6 will be shown and description will be omitted.

At Step S1702, the information processing apparatus 1600 acquires an analysis starting request. An equivalent processing to the Step S602 is executed.

At Step S1704, the information processing apparatus 1600 acquires analyzing condition setting. The manager 1699 operates a mouse, a keyboard or a touch panel to acquire the analyzing condition setting. An analyzing condition may be one of a period, an organization to which a target person belongs and a place or their combination. FIG. 18 is an explanatory diagram showing an example of an analyzing condition setting screen 1800. The analyzing condition setting screen 1800 has an analyzing period setting column 1810, an analyzing organization setting column 1820, an analyzing area setting column 1830, an analysis starting button 1840 and a reset button 1850. The analyzing period setting column 1810 is used for setting a period to be an analyzing target. The analyzing organization setting column 1820 is used for setting an organization to be the analyzing target. The analyzing area setting column 1830 is used for setting an area to be the analyzing target. Based on the operation for setting the analyzing period setting column 1810, the analyzing organization setting column 1820 and the analyzing area setting column 1830 in a selection of the analysis starting button 1840, the analyzing condition setting is acquired. It is also possible to set, as the analyzing condition, a name of an infection disease, an age and a job grade in addition to the period, the area and the organization.

At Step S1706, the log information acquiring module 110 acquires log information. An equivalent processing to the Step S604 is executed.

At Step S1708, an analyzing model generating module 122 generates an analyzing model. An equivalent processing to the Step S606 is executed.

At Step S1710, the analysis result generating module 124 generates an analysis result. An equivalent processing to the Step S608 is executed.

In the processings from the Step S1706 to the Step S1710, it is also possible to execute a processing for generating an analyzing model for all of action log data or a processing for setting, as a target, an object which is coincident with the analyzing condition acquired at the Step S1704 equivalently to the example of the processing according to the (1-A)th exemplary embodiment.

At Step S1712, the analysis result aggregating module 1610 aggregates an analysis result. Based on the analyzing condition acquired at the Step S1704, the analysis result is totalized.

Figure 19:
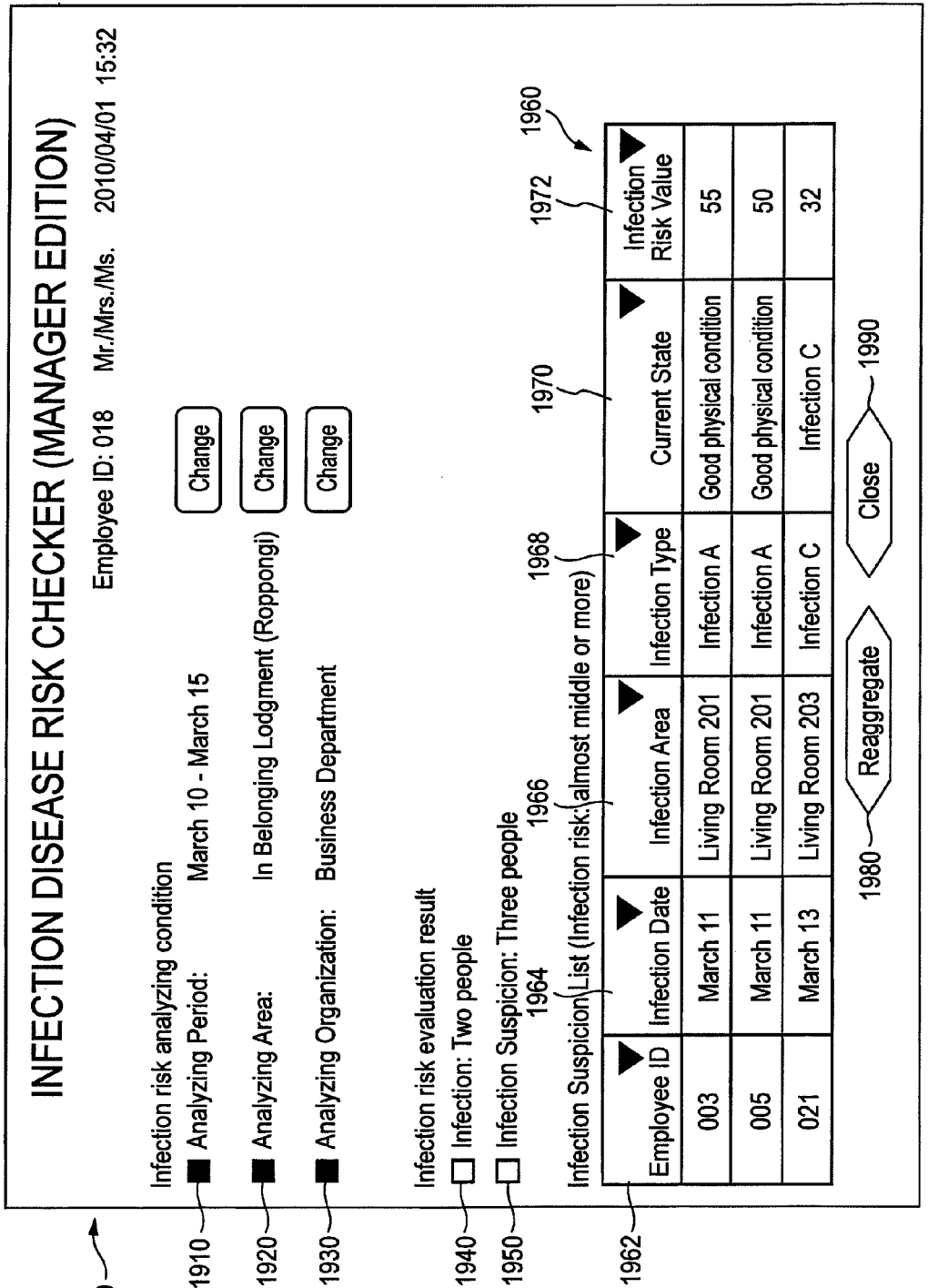
FIG. 19 is an explanatory diagram showing an example of an infection disease risk analyzing screen.

At Step S1714, the result presenting module 130 presents the analysis result. For example, as in an infection disease risk analyzing screen 1900 illustrated in FIG. 19, the analysis result is presented to a display device of an information processing apparatus which may be operated by the manager 1699. FIG. 19 is an explanatory diagram showing an example of the infection disease risk analyzing screen 1900. The infection disease risk analyzing screen 1900 has an analyzing period display region 1910 for presenting an infection risk analyzing condition, an analyzing area display region 1920, an analyzing organization display region 1930, an infection display region 1940 for presenting an infection risk evaluation result, an infection suspicion display region 1950, an infection suspicion list 1960, a reaggregating button 1980 and a closing button 1990. The analyzing period display region 1910, the analyzing area display region 1920 and the analyzing organization display region 1930 are columns for displaying the analyzing conditions acquired at the Step S1704 (which correspond to the analyzing period setting column 1810, the analyzing organization setting column 1820 and the analyzing area setting column 1830 which are illustrated in FIG. 18). More specifically, the infection display region 1940 and the infection suspicion display region 1950 are obtained by totalizing the number of people which is coincident with an extent of a possibility of an infection of the infection risk decision result column 1420 in the infection risk deciding table 1400. The infection suspicion list 1960 serves to present the details of a person classified into the infection suspicion display region 1950 and has an employee ID column 1962, an infection date column 1964, an infection area column 1966, an infection type column 1968, a current state column 1970, and an infection risk value column 1972. For each column, moreover, it is also possible to execute a processing such as a rearrangement based on sorting or filtering for fetching an object which is coincident with the condition.

At Step S1716, the analysis result aggregating module 1610 decides whether the aggregating condition is changed or not. If the aggregating condition is changed, the processings in and after the Step S1712 are executed. In the other cases, the processing is ended (Step S1799). For example, the analyzing period display region 1910, the analyzing area display region 1920 and the analyzing organization display region 1930 which are illustrated in FIG. 19 have changing buttons. If any of the changing buttons is selected, there is carried out such a display as to enable a change in the analyzing conditions. The case in which the reaggregating button 1980 is selected after the analyzing condition is changed corresponds to the case in which the aggregating condition is changed.

Figure 20:
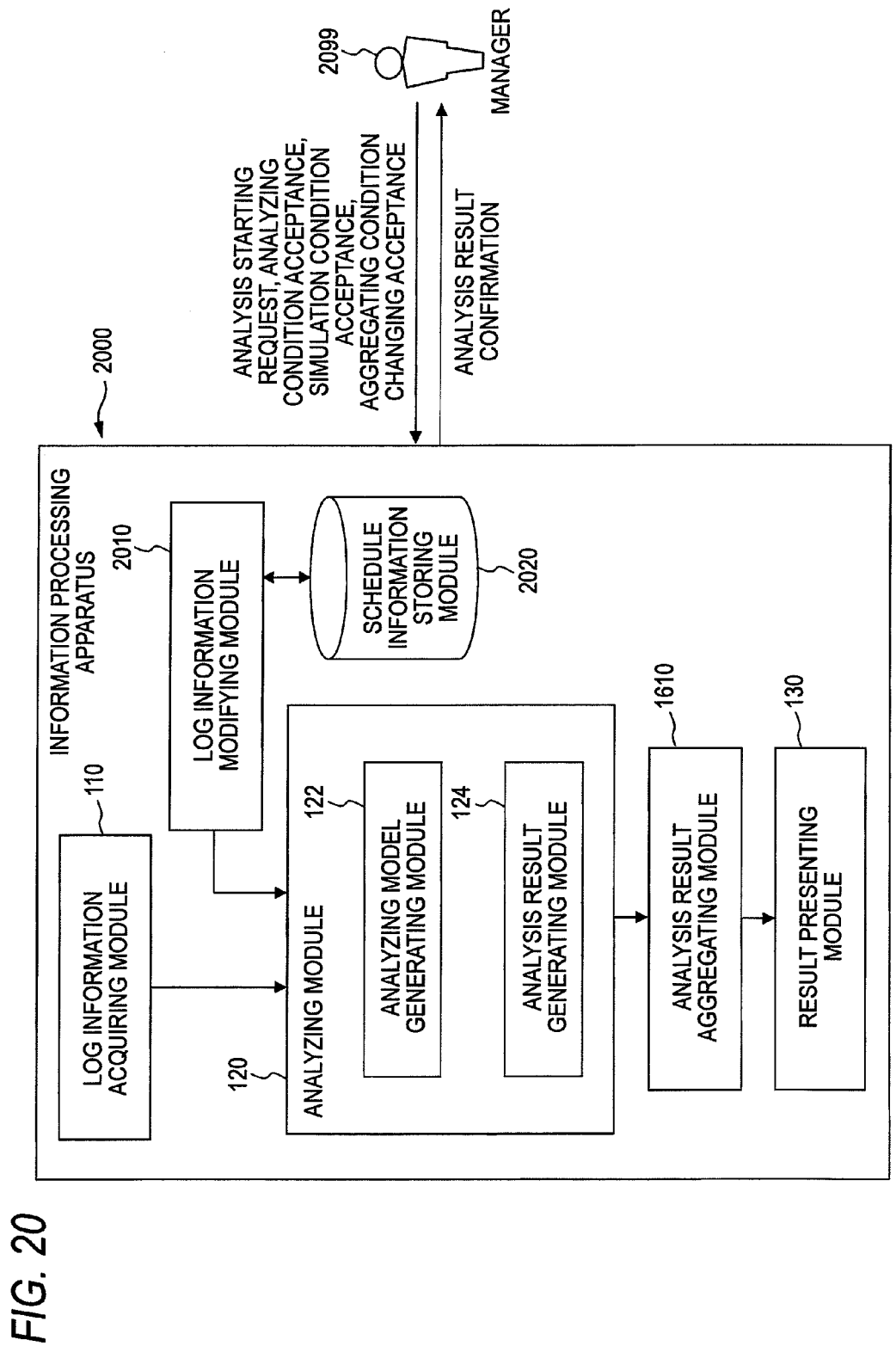
FIG. 20 is a diagram showing a conceptual module structure according to an example of a structure in accordance with a (1-C)th exemplary embodiment.

FIG. 20 is a diagram showing a conceptual module structure according to an example of a structure in accordance with the (1-C)th exemplary embodiment. An information processing apparatus 2000 has a log information acquiring module 110, an analyzing module 120, a log information modifying module 2010, a schedule information storing module 2020, an analysis result aggregating module 1610 and a result presenting module 130.

In the (1-C)th exemplary embodiment, past action log data are changed to carry out a simulation or schedule information to be a future schedule is used to carry out a simulation.

The log information modifying module 2010 is connected to the analyzing module 120 and the schedule information storing module 2020. The log information modifying module 2010 serves to modify one of a starting date and time of an event, an ending date and time of the event, and a place for an occurrence of the event which are included in action log data stored in an indoor action log DB 510, or their combination. Moreover, it is also possible to carry out a modification for adding schedule information about a target user through the schedule information storing module 2020 for storing schedule information about an event including at least a starting date and time of an event, an ending date and time of the event and a place for an occurrence of the event which are future schedules of the user. The modification includes a change and deletion of the stored action log data, and furthermore, a new addition of schedule information as action log data.

The schedule information storing module 2020 is connected to the log information modifying module 2010. The schedule information storing module 2020 stores schedule information, that is, information including at least the starting date and time of the event, the ending date and time of the event and the place for the occurrence of the event which are the future schedules of the user. The information in the schedule information storing module 2020 is acquired from a schedule DB 520.

Figure 21:
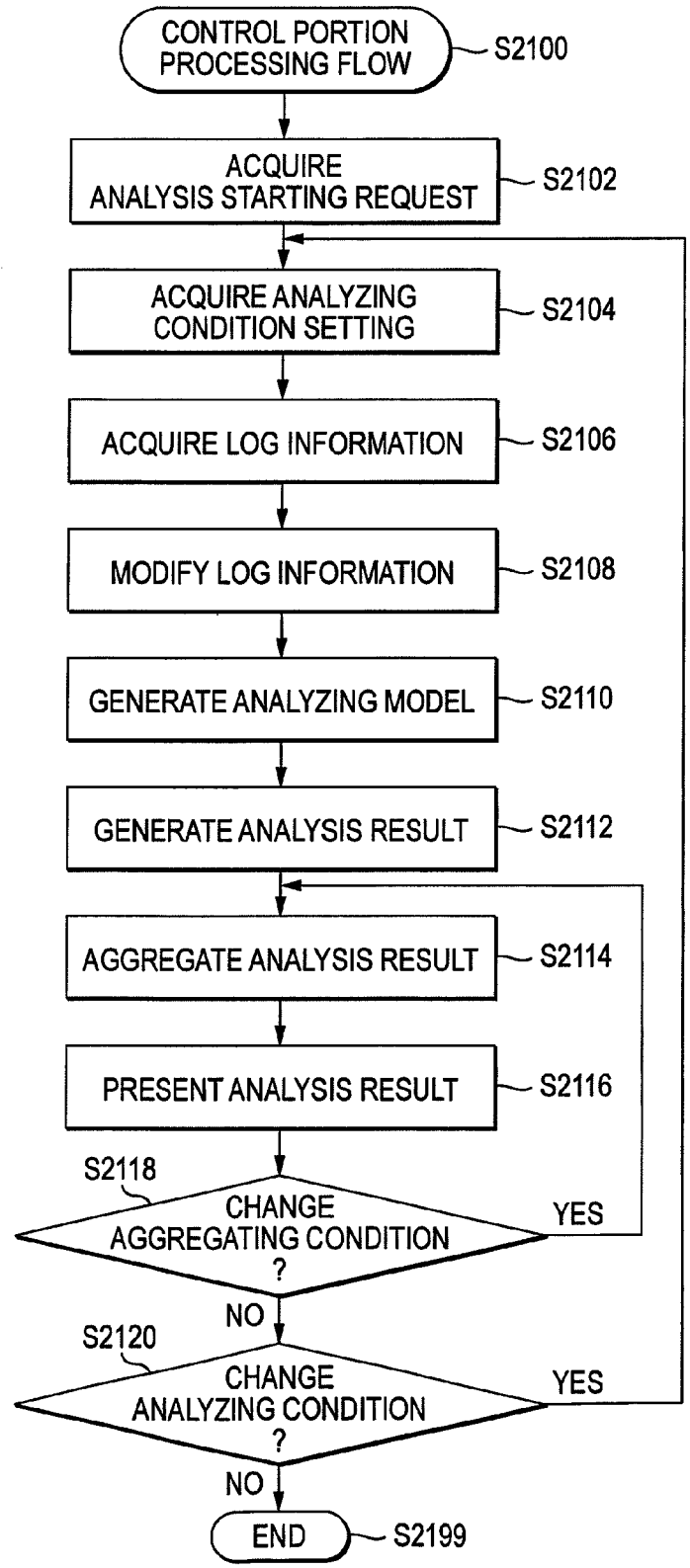
FIG. 21 is a flowchart showing an example of a processing according to the (1-C)th exemplary embodiment.

FIG. 21 is a flowchart showing an example of a processing according to the (1-C)th exemplary embodiment. In the case of the same processing as that in the flowchart showing the example of the processing according to the (1-B)th exemplary embodiment illustrated in FIG. 17, the steps illustrated in the example of FIG. 17 will be shown and description will be omitted.

At Step S2102, the information processing apparatus 2000 acquires an analysis starting request. An equivalent processing to the Step S1702 is executed.

At Step S2104, the information processing apparatus 2000 acquires analyzing condition setting. An equivalent processing to the Step S1704 is executed.

At Step S2106, the log information acquiring module 110 acquires log information. An equivalent processing to the Step S1706 is executed.

Figure 22:
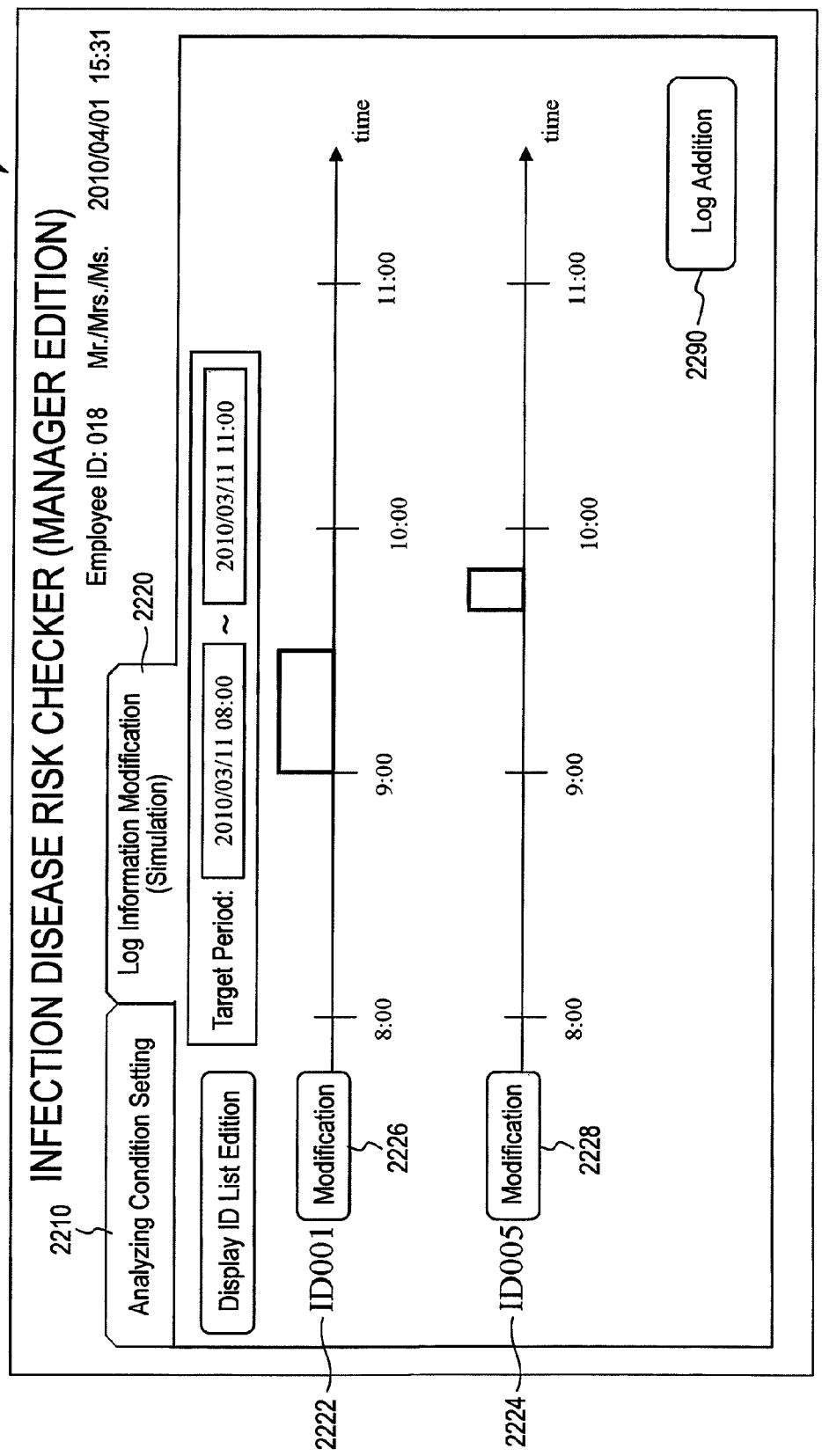
FIG. 22 is an explanatory diagram showing an example of an infection disease risk simulation screen.

At Step S2108, the log information modifying module 2010 modifies the log information. By operating a mouse, a keyboard or a touch panel through a manager 2099, a simulation condition is accepted and the action log data are modified. For example, a screen for setting the simulation condition includes an infection disease risk simulation screen 2200. FIG. 22 is an explanatory diagram showing an example of the infection disease risk simulation screen 2200. The infection disease risk simulation screen 2200 has an analyzing condition setting tab 2210 and a log information modifying (simulation) tab 2220. The log information modifying (simulation) tab 2220 has a target (ID001) log display region 2222 for presenting past action log data on a target person and a target (ID005) log display region 2224, a modifying button 2226 and a modifying button 2228 which serve to modify the action log data, and a log adding button 2290 for newly adding action log data based on schedule information. Although a date and time that a person enters a room and a date and time that the person leaves the room may be varied in the example of FIG. 22, it is also possible to additionally enable a change in the room or an infection state. In the case in which the log adding button 2290 is selected, moreover, the log information modifying module 2010 fetches schedule information about a target user from the schedule information storing module 2020 and adds the schedule information as the action log data.

At Step S2110, an analyzing model generating module 122 generates an analyzing model. An equivalent processing to the Step S1708 is executed.

At Step S2112, an analysis result generating module 124 generates an analysis result. An equivalent processing to the Step S1710 is executed.

At Step S2114, the analysis result aggregating module 1610 aggregates the analysis result. An equivalent processing to the Step S1712 is executed.

At Step S2116, the result presenting module 130 presents the analysis result. An equivalent processing to the Step S1714 is executed.

At Step S2118, the analysis result aggregating module 1610 decides whether an aggregating condition is changed or not. If the aggregating condition is changed, the processings in and after the Step S2114 are executed. In the other cases, the processing proceeds to Step S2120. An equivalent processing to the Step S1716 is executed.

At the Step S2120, the log information modifying module 2010 decides whether an analyzing condition is changed or not. If the analyzing condition is changed, the processings in and after the Step S2104 are executed. In the other cases, the processing is ended (Step S2199).

Although the analysis result aggregating module 1610 is used as is illustrated in FIG. 20 in the (1-C)th exemplary embodiment, it is also possible to eliminate the analysis result aggregating module 1610 and to connect the analyzing module 120 to the result presenting module 130. A general user may make use in place of the manager 2099 as in the (1-A)th exemplary embodiment.

In the first exemplary embodiment (including the (1-A)th exemplary embodiment, the (1-B)th exemplary embodiment and the (1-C)th exemplary embodiment), moreover, the infection risk is analyzed. However, it is also possible to analyze an evaluation value of an opportunity for meeting a certain person (a so-called opportunity loss). For example, it is also possible to obtain an analysis result of "I will be able to meet Mr. N who is a division manager if I reach the meeting room two minutes earlier".

Figure 23:
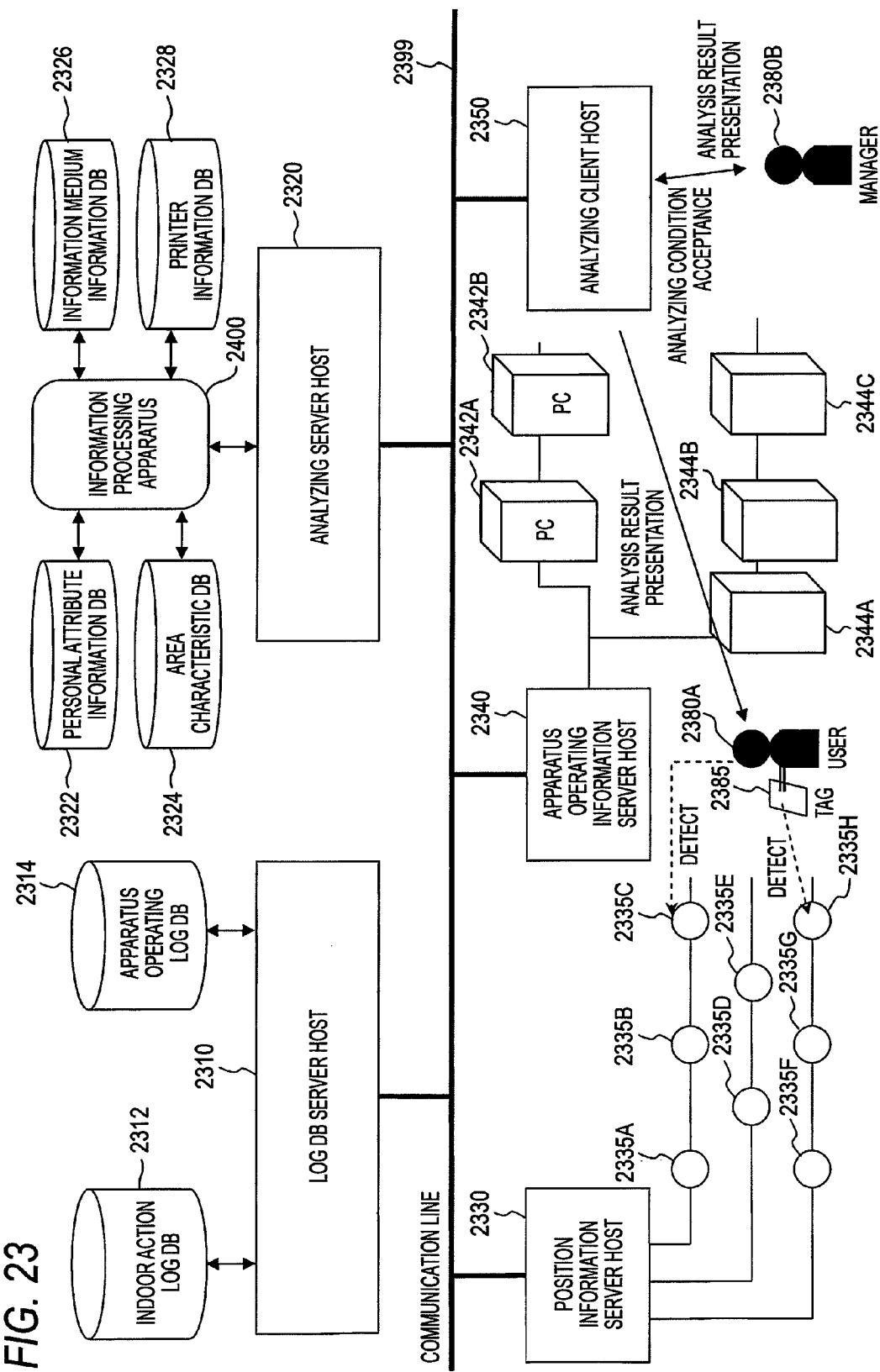
FIG. 23 is an explanatory diagram showing an example of a system structure in the case in which a second exemplary embodiment is materialized.

FIG. 23 is an explanatory diagram showing an example of a system structure in the case in which a second exemplary embodiment is materialized. In the second exemplary embodiment, there is analyzed a risk of an information leakage which is caused by stealing a glance at an output result of an image output device through an analyzing target.

A log DB server host 2310, an analyzing server host 2320, a position information server host 2330, an apparatus operating information server host 2340 and an analyzing client host 2350 are connected through a communication line 2399, respectively. The log DB server host 2310 is connected to an indoor action log DB 2312 and an apparatus operating log DB 2314. The analyzing server host 2320 is connected to an information processing apparatus 2400. The information processing apparatus 2400 will be described below with reference to FIG. 24. It is also possible to employ an information processing apparatus 3600 illustrated in FIG. 36 or an information processing apparatus 4000 illustrated in FIG. 40 in place of the information processing apparatus 2400. The information processing apparatus 2400 is connected to the analyzing server host 2320, a personal attribute information DB 2322, an area characteristic DB 2324, an information medium information DB 2326 and a printer information DB 2328. The position information server host 2330 is connected to position sensors 2335A to 2335H. The apparatus operating information server host 2340 is connected to PCs 2342A and 2342B and composite machines 2344A, 2344B and 2344C. While the composite machine is an image processing apparatus having at least two functions of a scanner, a printer, a composite machine and a fax, it represents an example of an image output device.

A user 2380A holds a tag 2385 (for example, active RFID (Radio Frequency IDentification)). The tag 2385 is detected by the position sensors 2335A to 2335H. Each position sensor reads user information indicative of a user stored in the tag 2385 (for example, an employee ID (IDentification)), and the user information is stored in the position information server host 2330 together with a detecting date and time and a position of the position sensor itself. For example, in the case in which the position sensor is attached to each room, action log data indicative of any person, any time, and any room in which the person stays are collected into the position information server host 2330. Then, the collected action log data are transferred to the log DB server host 2310 and are stored in the indoor action log DB 2312.

The apparatus operating information server host 2340 detects an operating situation of a PC 2342A or the composite machine 2344A (for example, a transmission of an output instruction from the PC 2342A to the composite machine 2344A, a print carried out by the composite machine 2344A or a collection of the printed matter) and transfers the detected information as apparatus operating log data to the log DB server host 2310, and the apparatus operating log data are stored in the apparatus operating log DB 2314.

The analyzing client host 2350 accepts an operating instruction to be an analysis starting request given by the user 2380A and transfers the operating instruction to the analyzing server host 2320, and makes the information processing apparatus 2400 analyze a risk of an information leakage caused by stealing a glance at an output result of an image output device, for example. The information processing apparatus 2400 carries out an analysis by using data in the personal attribute information DB 2322, the area characteristic DB 2324, the information medium information DB 2326 and the printer information DB 2328 or data in the indoor action log DB 2312 and the apparatus operating log DB 2314 and presents an analysis result to the analyzing client host 2350 through the analyzing server host 2320, and informs the user 2380A of the analysis result. Moreover, the analyzing client host 2350 accepts an analyzing condition given by a manager 2380B and transfers the analyzing condition to the analyzing server host 2320, and makes the information processing apparatus 2400 analyze the risk of the information leakage caused by stealing a glance at the output result of the image output device on the analyzing condition, for example. The information processing apparatus 2400 carries out an analysis by using the data in the personal attribute information DB 2322, the area characteristic DB 2324, the information medium information DB 2326 and the printer information DB 2328 or the data in the indoor action log DB 2312 and the apparatus operating log DB 2314 depending on the analyzing condition, and presents an analysis result to the analyzing client host 2350 through the analyzing server host 2320 and informs the manager 2380B of the analysis result.

Figure 24:
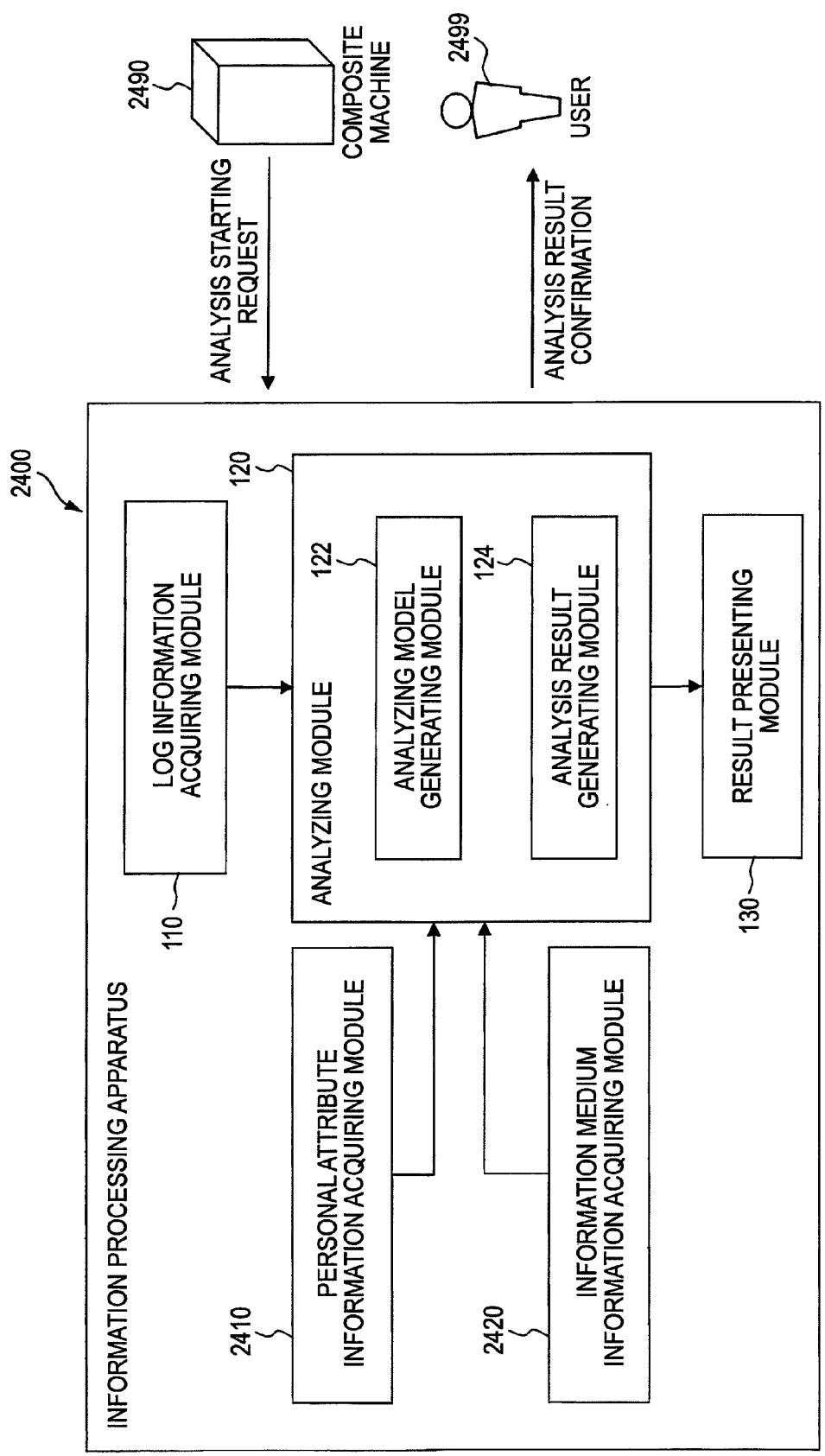
FIG. 24 is a diagram showing a conceptual module structure according to an example of a structure in accordance with a (2-A)th exemplary embodiment.

FIG. 24 is a diagram showing a conceptual module structure according to an example of a structure in accordance with the (2-A)th exemplary embodiment. An information processing apparatus 2400 has a log information acquiring module 110, an analyzing module 120, a personal attribute information acquiring module 2410, an information medium information acquiring module 2420, and a result presenting module 130.

The log information acquiring module 110 is connected to the analyzing module 120. The log information acquiring module 110 acquires recording information about a target event from an event recording information storage device for storing recording information about an event including at least a starting date and time of an event, an ending date and time of the event and a place for an occurrence of the event (which will be hereinafter referred to as log information). For example, the log information acquiring module 110 acquires log information about a position or state of a person or thing at a certain time from the indoor action log DB 2312 and the apparatus operating log DB 2314 which are illustrated in FIG. 23. Attribute information about a person or a thing may be acquired, together with the log information, from the personal attribute information DB 2322, the area characteristic DB 2324, the information medium information DB 2326 or the printer information DB 2328 which is illustrated in FIG. 23.

If an analyzing target is a risk of an information leakage caused by stealing a glance at an output result of an image output device (for example, a printer or a display), an action for a certain person to enter or leave a certain room corresponds to a first event. An output of a certain image output device corresponds to a second event. In this case, a date and time that the person enters the room corresponds to a starting date and time of the first event. A date and time that the person leaves the room corresponds to an ending date and time of the first event. The room corresponds to a place for an occurrence of the first event. A date and time that the image output device carries out the output corresponds to a starting date and time of the second event. A date and time that a printed matter output from the image output device is collected corresponds to an ending date and time of the second event. A room in which the image output device is installed corresponds to a place for an occurrence of the second event.

The analyzing module 120 has an analyzing model generating module 122 and an analysis result generating module 124. The analyzing module 120 is connected to the log information acquiring module 110, the personal attribute information acquiring module 2410, the information medium information acquiring module 2420 and the result presenting module 130. The analyzing module 120 carries out an analysis by using the log information.

The analyzing model generating module 122 sets, as a starting date and time of a model, a date and time before a predetermined period since a starting date and time in recording information about an event acquired by the log information acquiring module 110, sets, as an ending date and time of the model, a date and time after a predetermined period since an ending date and time in the recording information about the event, and generates a model including at least influence information for calculating an influence of the event. The analyzing model generating module 122 generates an analyzing model obtained by adding analyzing model information meeting an analyzing purpose to the acquired log information.

The analysis result generating module 124 analyzes an influence of the first event and the second event based on a period for which a period determined by starting and ending dates and times of the model of the first event that is generated by the analyzing model generating module 122 overlaps with a period determined by starting and ending dates and times of the model of the second event that is generated by the analyzing model generating module 122, and influence information about the model of the first event or influence information about the model of the second event. The analysis result generating module 124 generates an analysis result meeting an analyzing purpose from the analyzing model generated by the analyzing model generating module 122.

The second event occurs in the same place as the place in which the first event occurs. In other words, the second event corresponds to the case in which an image output device provided in a room that a target person enters carries out an output operation.

The result presenting module 130 is connected to the analyzing module 120. The result presenting module 130 presents the analysis result obtained by the analysis result generating module 124.

The personal attribute information acquiring module 2410 is connected to the analyzing module 120. Personal attribute information is acquired from the personal attribute information DB 2322 illustrated in FIG. 23.

The information medium information acquiring module 2420 is connected to the analyzing module 120. Information medium information is acquired from the information medium information DB 2326 illustrated in FIG. 23.

The analyzing model generating module 122 or the analysis result generating module 124 in the analyzing module 120 may execute the processing by using the personal attribute information acquired by the personal attribute information acquiring module 2410 or the information medium information acquired by the information medium information acquiring module 2420.

A request for starting an analysis may be given to the information processing apparatus 2400 through an operation over a touch panel of a composite machine 2490 by a user 2499. Moreover, the result presenting module 130 may present the analysis result to the touch panel of the composite machine 2490, thereby informing the user 2499 of the analysis result. Moreover, the composite machine 2490 may transmit an analysis starting request of an information leakage risk to the information processing apparatus 2400 when a left print period (a period for which an output print medium is not collected) occurs beyond a predetermined period.

Figure 25:
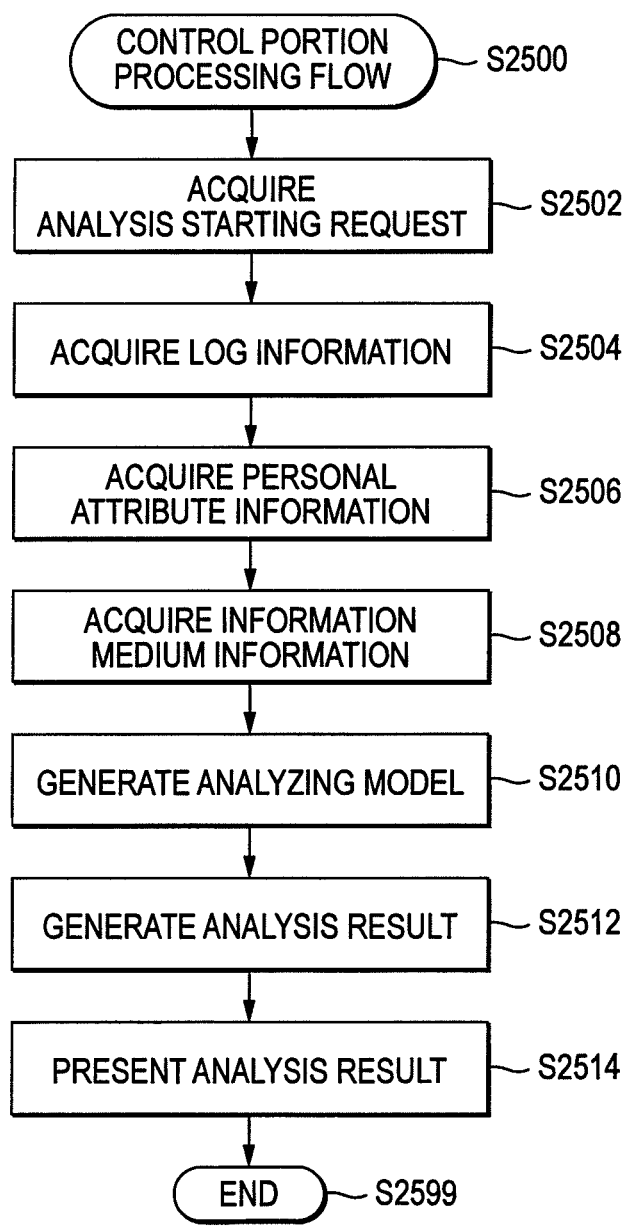
FIG. 25 is a flowchart showing an example of a processing according to the (2-A)th exemplary embodiment.

FIG. 25 is a flowchart showing an example of a processing according to the (2-A)th exemplary embodiment.

At Step S2502, the information processing apparatus 2400 acquires an operating instruction to be an analysis starting request through an operation of a mouse, a keyboard or a touch panel by a user.

At Step S2504, the log information acquiring module 110 acquires log information from the indoor action log DB 2312 or the apparatus operating log DB 2314. The indoor action log DB 2312 stores log data to be a record of a past action of each person, particularly, log data catching an actual result of an indoor action. For example, an action log table 2600 illustrated in FIG. 26 is stored. FIG. 26 is an explanatory diagram showing an example of a data structure of the action log table 2600. The action log table 2600 has a starting time column 2610, an ending time column 2620, an employee ID column 2630, and a detection area column 2640. The starting time column 2610 stores a date and time that a user of the employee ID column 2630 enters a room of the detection area column 2640. The ending time column 2620 stores a date and time that the user of the employee ID column 2630 leaves the room of the detection area column 2640. The employee ID column 2630 stores user information indicative of a target user. For example, an employee ID is stored. The detection area column 2640 stores area information indicative of an area (a place) in which the user (accurately, a tag 2385 held by the user) is detected. For example, a name of a meeting room is stored.

The apparatus operating log DB 2314 stores log data to be a record of a past action of each apparatus, particularly, log data to be actual results of starting and ending times that a print medium output by an image output device is left. For example, a print log table 2900 illustrated in FIG. 29 is stored. FIG. 29 is an explanatory diagram showing an example of a data structure of the print log table 2900. The print log table 2900 has a leaving starting time column 2910, a leaving ending time column 2920, a document ID column 2930, a print indicator ID column 2940 and a printer ID column 2950. The leaving starting time column 2910 stores a date and time that the output is ended. The leaving ending time column 2920 stores a date and time that the output print medium is collected. The document ID column 2930 stores a document ID indicative of an output electronic document. The print indicator ID column 2940 stores a print indicator ID indicative of a person giving an instruction for an output. The printer ID column 2950 stores a printer ID indicative of the image output device carrying out the output. The image output device generates log data in the print log table 2900. For example, a date and time that the output is ended is stored as the leaving starting time, and the fact that the output print medium is collected (an output paper is taken away from the image output device) is detected by means of a sensor and a date and time thereof is stored as a leaving ending time.

Figure 28:
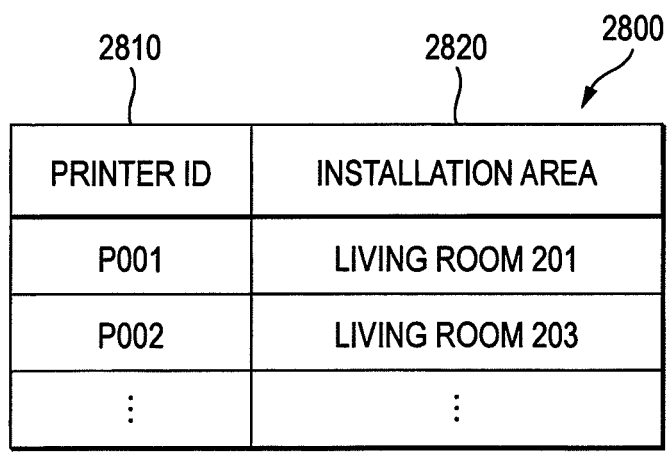
FIG. 28 is an explanatory diagram showing an example of a data structure of a printer information table.

Moreover, an area in which the image output device is installed may be fetched from the printer information DB 2328 based on a printer ID in the printer ID column 2950 of the print log table 2900. The printer information DB 2328 stores a printer information table 2800, for example. FIG. 28 is an explanatory diagram showing an example of a data structure of the printer information table 2800. The printer information table 2800 has a printer ID column 2810 and an installation area column 2820. The printer ID column 2810 stores a printer ID indicative of the image output device. The installation area column 2820 stores an area in which the image output device is installed.

Figure 27:
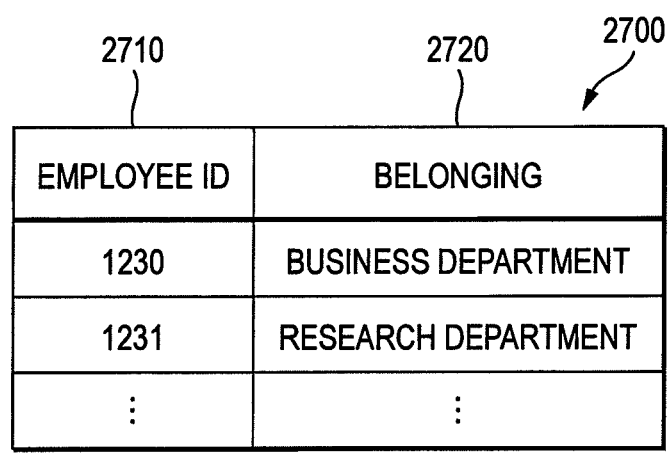
FIG. 27 is an exemplary diagram showing an example of a data structure of a personal attribute information table.

At Step S2506, the personal attribute information acquiring module 2410 acquires personal attribute information. For example, based on an employee ID in the employee ID column 2630 of the action log table 2600, an organization to which the employee belongs may be fetched from the personal attribute information DB 2322. The personal attribute information DB 2322 stores a personal attribute information table 2700, for example. FIG. 27 is an explanatory diagram showing an example of a data structure of the personal attribute information table 2700. The personal attribute information table 2700 has an employee ID column 2710 and a belonging column 2720. The employee ID column 2710 stores an employee ID indicative of a user. The belonging column 2720 stores an organization to which the user belongs.

Figure 30:
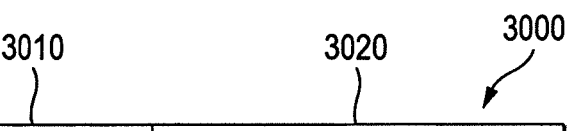
FIG. 30 is an explanatory diagram showing an example of a data structure of an information medium information table.

At Step S2508, the information medium information acquiring module 2420 acquires information medium information. For example, based on a document ID in the document ID column 2930 of the print log table 2900, a disclosure range of the document may be fetched from the information medium information DB 2326. The information medium information DB 2326 stores an information medium information table 3000, for example. FIG. 30 is an explanatory diagram showing an example of a data structure of the information medium information table 3000. The information medium information table 3000 has a document ID column 3010 and a disclosure range column 3020. The document ID column 3010 stores a document ID indicative of an electronic document. The disclosure range column 3020 stores a disclosure range of the document.

At Step S2510, the analyzing model generating module 122 generates an analyzing model. The analyzing model is generated based on the action log data (the action log table 2600) acquired at the Step S2504, log data on an operation of an apparatus (the print log table 2900), the personal attribute information (the personal attribute information table 2700) acquired at the Step S2506, the information medium information (the information medium information table 3000) acquired at the Step S2508, and a risk evaluation maximum value deciding table 3100. FIG. 31 is an explanatory diagram showing an example of a data structure of the risk evaluation maximum value deciding table 3100. The risk evaluation maximum value deciding table 3100 has a disclosure range/belonging column 3110, an in-specific department column 3120, an in-house column 3130, an outside company (non-competition) column 3140, and an outside company (competition) column 3150. The disclosure range/belonging column 3110 stores an organization to be a disclosure range of a document. The in-specific department column 3120 stores a maximum risk value in the case in which the document is disclosed to a specific department. The in-house column 3130 stores a maximum risk value in the case in which the document is disclosed to an inside of a company. The outside company (non-competition) column 3140 stores a maximum risk value in the case in which the document is disclosed to the outside of the company (non-competition). The outside company (competition) column 3150 stores a maximum risk value in the case in which the document is disclosed to the outside of the company (competition). For example, it is indicated that a maximum risk value is zero when the document is in a specific department (it is preferable to acquire an organization in the corresponding disclosure range column 3020 of the information medium information table 3000 based on the document ID in the document ID column 2930 of the print log table 2900) and is disclosed to the specific department, is 30 when the document is disclosed to the inside of the company, is 50 when the document is disclosed to the outside of the company (non-competition), and is 100 when the document is disclosed to the outside of the company (competition) based on a first line of the risk evaluation maximum value deciding table 3100.

For example, an analyzing model to be generated includes an action log information leakage risk analyzing model table 3300 and an apparatus operating log information leakage risk analyzing model table 3400. FIG. 33 is an explanatory diagram showing an example of a data structure of the action log information leakage risk analyzing model table 3300. The action log information leakage risk analyzing model table 3300 has a starting time column 3310, an ending time column 3320, an employee ID column 3330, a detection area column 3340, a risk generating time column 3350, a risk disappearing time column 3360, and a risk evaluation maximum value column 3370. The starting time column 3310 to the detection area column 3340 correspond to the staring time column 2610 to the detection area column 2640 in the action log table 2600, and store starting times, ending times, employee IDs and detection areas which are acquired respectively. The risk generating time column 3350 to the risk evaluation maximum value column 3370 are added as analyzing models. The risk generating time column 3350 stores a date and time before a predetermined period (in this case, three minutes) since the starting time stored in the starting time column 2610. The risk disappearing time column 3360 stores a date and time after a predetermined period since the ending time stored in the ending time column 2620. The risk evaluation maximum value column 3370 stores a risk evaluation maximum value to be influence information for calculating an influence of an event.

FIG. 34 is an explanatory diagram showing an example of a data structure of the apparatus operating log information leakage risk analyzing model table 3400. The apparatus operating log information leakage risk analyzing model table 3400 has a leaving starting time column 3410, a leaving ending time column 3420, a document ID column 3430, a print indicator ID column 3440, a printer ID column 3450, an installation area column 3460, a risk generating time column 3470, a risk disappearing time column 3480, and a risk evaluation maximum value column 3490. The leaving starting time column 3410 to the printer ID column 3450 correspond to the leaving starting time column 2910 to the printer ID column 2950 in the print log table 2900, and store leaving starting times, leaving ending times, document IDs, print indicator IDs and printer IDs which are acquired respectively. The installation area column 3460 to the risk evaluation maximum value column 3490 are added as analyzing models. The installation area column 3460 uses the printer information table 2800 to store an area in which an image output device in the printer ID column 3450 is installed. The risk generating time column 3470 stores a date and time before a predetermined period (in this case, one minute) since the starting time stored in the leaving starting time column 2910. The risk disappearing time column 3480 stores a date and time after a predetermined period (in this case, zero second) since the ending time stored in the leaving ending time column 2920. The risk evaluation maximum value column 3490 stores a risk evaluation maximum value to be influence information for calculating an influence of an event.

At Step S2512, the analysis result generating module 124 generates an analysis result. For example, a risk evaluation value of the image output device is shown in a graph according to an example of FIG. 32. From a time (ts') that the image output device starts a printing operation to a time (ts, a leaving starting time) that the printing operation is ended, the risk evaluation value is increased. From the time (ts, the leaving starting time) that the printing operation is ended to a time (te, a leaving ending time) that a print medium is collected, there is obtained a risk evaluation maximum value in the case in which a document is left. The risk evaluation value is decreased till a time (te') after a predetermined period since the time (te, the leaving ending time) that the print medium is collected. A period from the time (ts') that the image output device starts the printing operation to the time (ts, the leaving starting time) that the printing operation is ended may be calculated based on the number of sheets of a document to be printed or a capability of the image output device. The risk evaluation maximum value (the risk evaluation maximum value deciding table 3100) is determined by a combination of an organization (the personal attribute information table 2700) to which a person entering an area having the image output device belongs and a disclosure range (the information medium information table 3000) of the output document.

A risk value of an information leakage caused by stealing a glance at an output result of the image output device is obtained by calculating a product of a risk evaluation maximum value at a time that an analyzing model of the image output device overlaps with a risk analyzing model of a user staying in the area having the image output device on a time base (the risk evaluation maximum value column 3370 of the action log information leakage risk analyzing model table 3300 and the risk evaluation maximum value column 3490 of the apparatus operating log information leakage risk analyzing model table 3400). In addition, it is also possible to obtain an area of a part in which the analyzing models overlap with each other.

At Step S2514, the result presenting module 130 presents the analysis result. For example, an analysis result notifying screen 3500 shown in FIG. 35 is presented to a print indicator through a touch panel of the image output device or a display device of an information processing apparatus such as a PC giving an output instruction.

Figure 36:
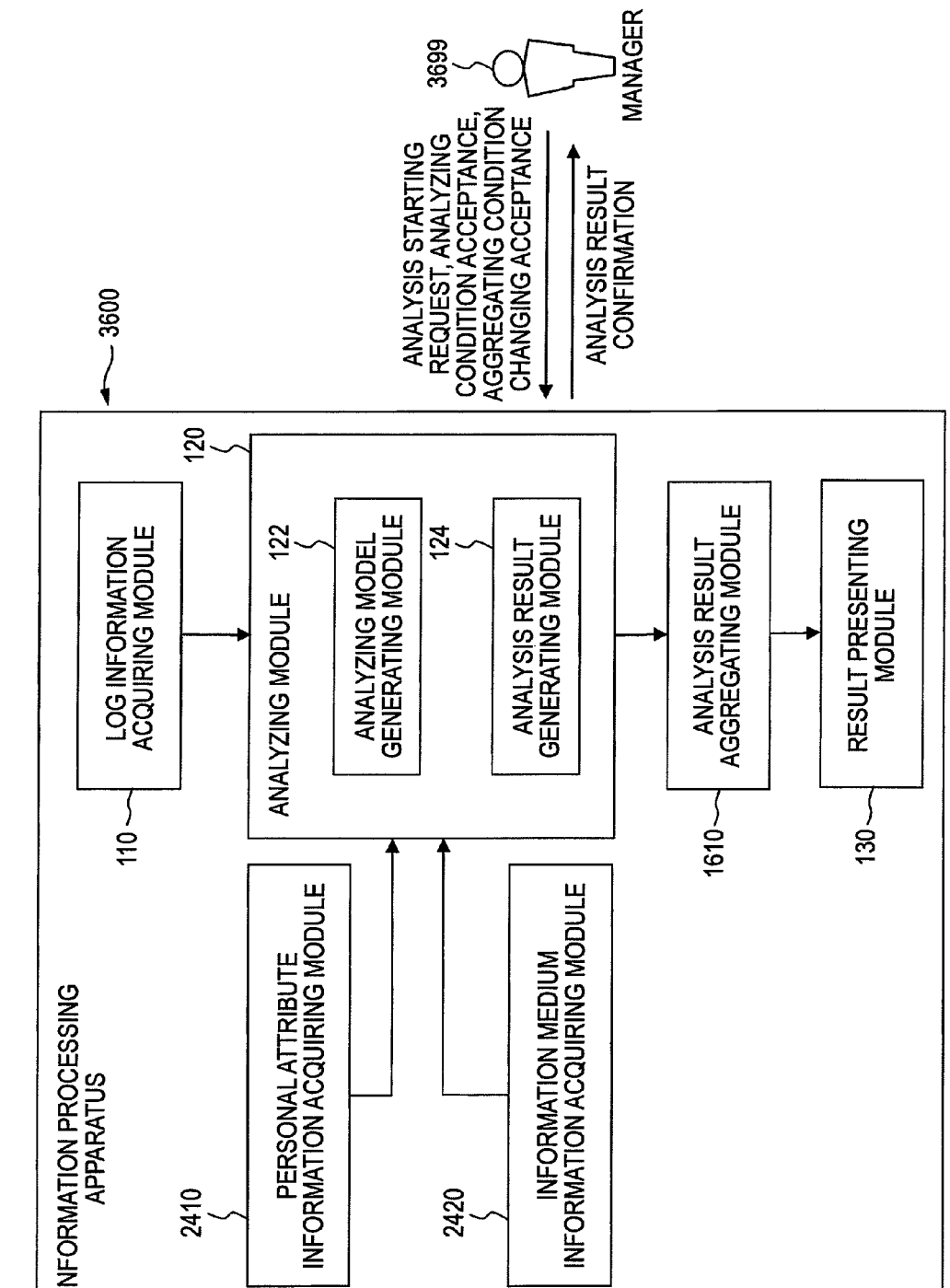
FIG. 36 is a diagram showing a conceptual module structure according to an example of a structure in accordance with a (2-B)th exemplary embodiment.

FIG. 36 is a diagram showing a conceptual module structure according to an example of a structure in accordance with the (2-B)th exemplary embodiment. An information processing apparatus 3600 has a log information acquiring module 110, an analyzing module 120, a personal attribute information acquiring module 2410, an information medium information acquiring module 2420, an analysis result aggregating module 1610, and a result presenting module 130. The same types of portions as those in the (2-A)th exemplary embodiment have the same reference numerals and repetitive description will be omitted (and so forth).

The user according to the (2-A)th exemplary embodiment is a general user giving an output instruction and serves to present an analysis result of a risk of the user himself (herself). The user according to the (2-B)th exemplary embodiment is a manager, and does not present an analysis result of a risk of a specific person but an analysis result of a risk of people belonging to a certain organization, for example.

For this purpose, the information processing apparatus 3600 acquires an analyzing condition, an analysis starting request or an aggregating condition change which is an operating instruction through an operation of a mouse, a keyboard or a touch panel by a manager 3699.

The analysis result aggregating module 1610 is connected to the analyzing module 120 and the result presenting module 130, and totalizes an analysis result obtained by an analysis result generating module 124 based on the operating instruction of the manager 3699. For example, the totalization may be carried out based on one of a period, an organization to which a target person belongs, an area in which an image output device is installed and a printed document or their combination.

Figure 37:
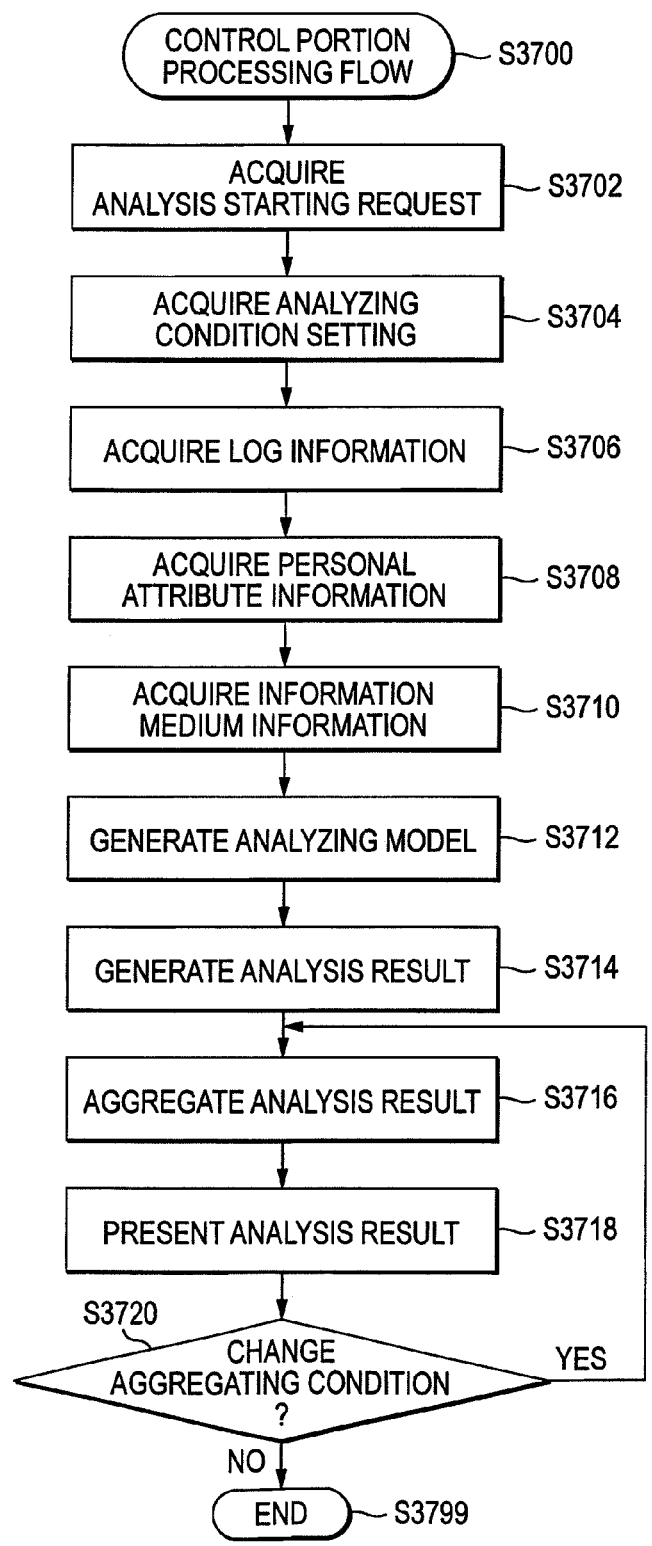
FIG. 37 is a flowchart showing an example of a processing according to the (2-B)th exemplary embodiment.

FIG. 37 is a flowchart showing an example of a processing according to the (2-B)th exemplary embodiment. In the case of the same processing as that in the flowchart showing the example of the processing according to the (2-A)th exemplary embodiment illustrated in FIG. 25, the steps according to the example of FIG. 25 will be shown and description will be omitted.

At Step S3702, the information processing apparatus 3600 acquires an analysis starting request. An equivalent processing to the Step S2502 is executed.

Figure 38:
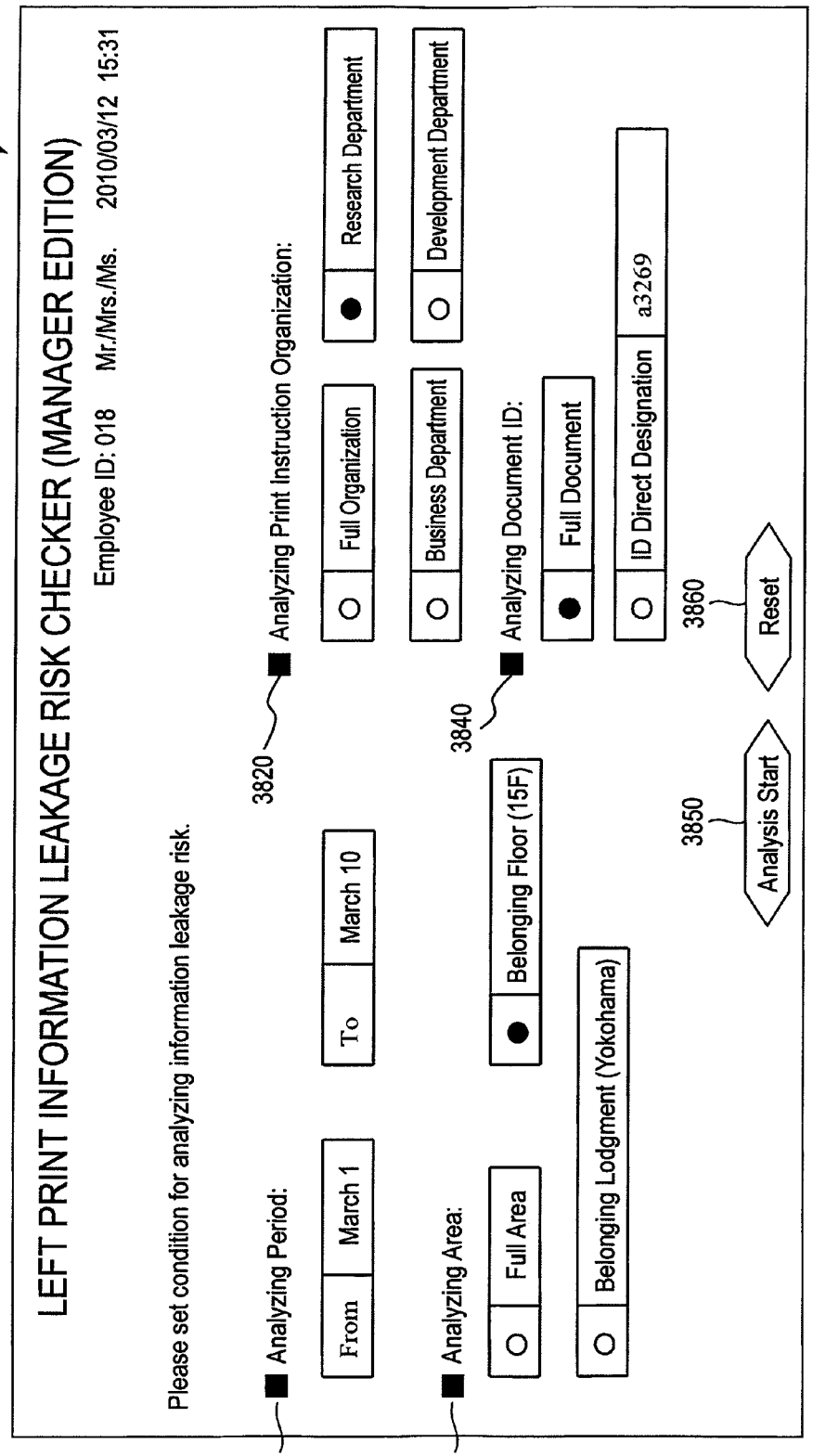
FIG. 38 is an explanatory diagram showing an example of an analyzing condition setting screen.

At Step S3704, the information processing apparatus 3600 acquires analyzing condition setting. The analyzing condition setting is acquired through the operation of the mouse, the keyboard or the touch panel by the manager 3699. As an analyzing condition, it is also possible to employ one of the period, the organization to which the target person belongs, the area in which the image output device is installed and the printed document or their combination. FIG. 38 is an explanatory diagram showing an example of an analyzing condition setting screen 3800. The analyzing condition setting screen 3800 has an analyzing period setting column 3810, an analyzing print instruction organization setting column 3820, an analyzing area setting column 3830, an analyzing document ID setting column 3840, an analysis starting button 3850, and a reset button 3860. In the analyzing condition setting screen 3800, the analyzing period setting column 3810 serves to set a period to be an analyzing target. The analyzing print instruction organization setting column 3820 serves to set an organization to be an analyzing target to which a person giving a print instruction belongs. The analyzing area setting column 3830 serves to set an area to be an analyzing target in which the image output device is installed. The analyzing document ID setting column 3840 serves to set an output electronic document. The analyzing condition setting is acquired based on setting of the analyzing period setting column 3810, the analyzing print instruction organization setting column 3820, the analyzing area setting column 3830 and the analyzing document ID setting column 3840 in a selection of the analysis starting button 3850. In addition to the period, the area, the organization and the document ID, it is also possible to set, as the analyzing condition, a job type and job grade of a user giving an output instruction, a printer ID, a document disclosure range and a document type.

At Step S3706, the log information acquiring module 110 acquires log information. An equivalent processing to the Step S2504 is executed.

At Step S3708, the personal attribute information acquiring module 2410 acquires personal attribute information. An equivalent processing to the Step S2506 is executed.

At Step S3710, the information medium information acquiring module 2420 acquires information medium information. An equivalent processing to the Step S2508 is executed.

At Step S3712, an analyzing model generating module 122 generates an analyzing model. An equivalent processing to the Step S2510 is executed.

At Step S3714, the analysis result generating module 124 generates an analysis result. An equivalent processing to the Step S2512 is executed.

At Step S3716, the analysis result is aggregated. Based on the analyzing condition acquired at the Step S3704, the analysis result is totalized.

Figure 39:
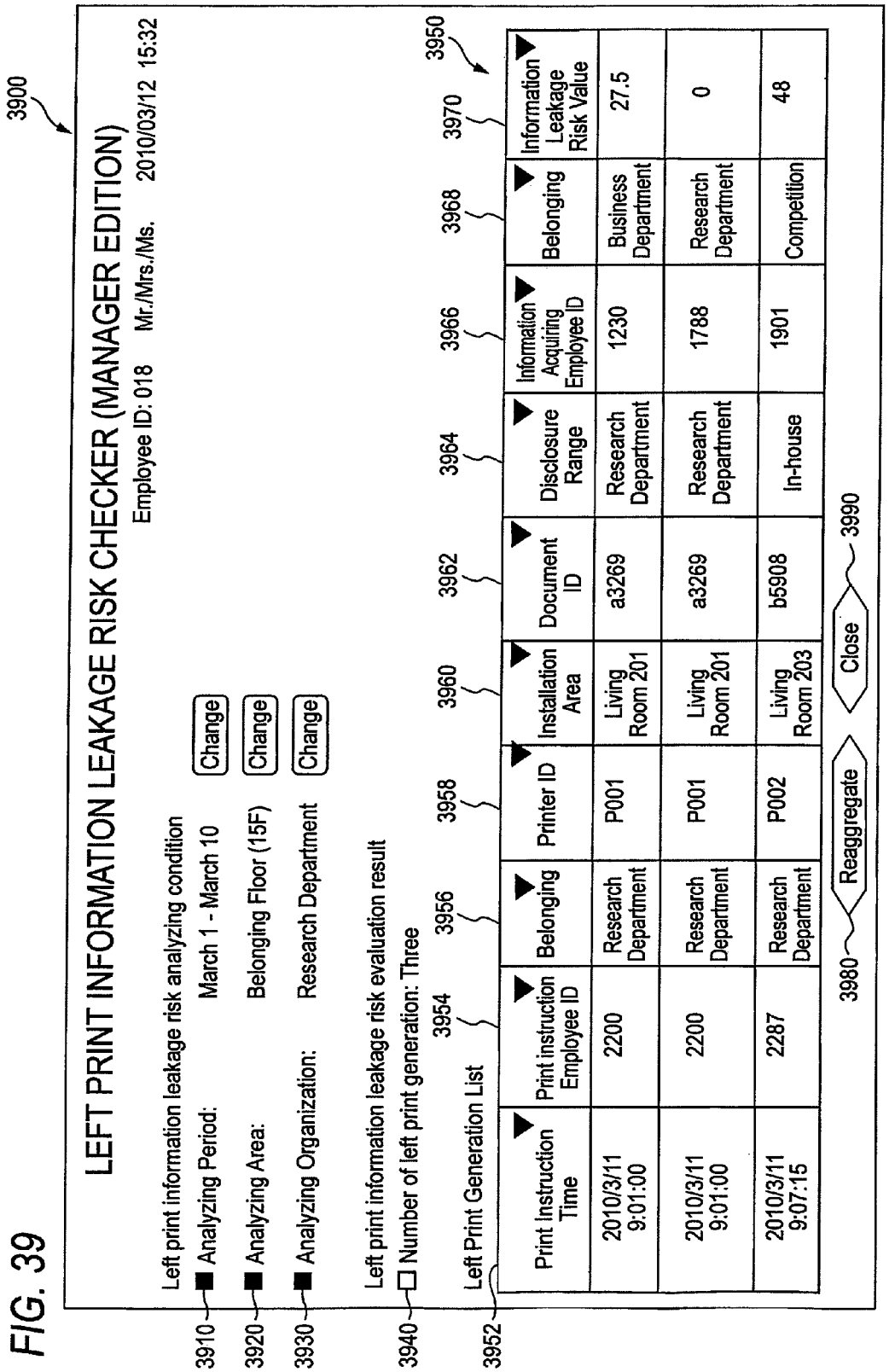
FIG. 39 is an explanatory diagram showing an example of a post-evaluating screen of an information leakage caused by a left print.

At Step S3718, the result presenting module 130 presents the analysis result. For example, as in a post-evaluation screen 3900 for an information leakage caused by a left print illustrated in FIG. 39, the analysis result is presented to a display device of an information processing apparatus which may be operated by the manager 3699. FIG. 39 is an explanatory diagram showing an example of the post-evaluation screen 3900 for the information leakage caused by the left print. The post-evaluation screen 3900 for the information leakage caused by the left print has an analyzing period display region 3910, an analyzing area display region 3920 and an analyzing organization display region 3930 which serve to present a risk analyzing condition, a left print generation number display region 3940 and a left print generation list 3950 which serve to present a risk evaluation result, a reaggregating button 3980, and a closing button 3990. The analyzing period display region 3910, the analyzing area display region 3920 and the analyzing organization display region 3930 serve to present the analyzing condition acquired at the Step S3704 (which correspond to the analyzing period setting column 3810, the analyzing area setting column 3830 and the analyzing print instruction organization setting column 3820 illustrated in FIG. 38). As a matter of course, it is also possible to provide a column for presenting a document ID as an analyzing target (which corresponds to the analyzing document ID setting column 3840 illustrated in FIG. 38). The left print generation number display region 3940 is a column for displaying the number of times that a collection is not carried out immediately after an output, and specifically, indicates the number of times of a coincidence with the analyzing condition in the print log table 2900. The left print generation list 3950 serves to present the detail of an item of the left print generation number display region 3940, and has a print instruction time column 3952, a print instruction employee ID column 3954, a belonging column 3956, a printer ID column 3958, an installation area column 3960, a document ID column 3962, a disclosure range column 3964, an information acquiring employee ID column 3966, a belonging column 3968, and an information leakage risk value column 3970. Moreover, it is also possible to enable an execution of a processing such as a rearrangement based on sorting or filtering for fetching an object which is coincident with the condition for each column.

At Step S3720, it is decided whether the aggregating condition is changed or not. If the aggregating condition is changed, the processings in and after the Step S3716 are executed. In the other cases, the processing is ended (Step S3799). For example, the analyzing period display region 3910, the analyzing area display region 3920 and the analyzing organization display region 3930 which are illustrated in FIG. 39 have changing buttons. If any of the changing buttons is selected, there is carried out such a display as to enable a change in the analyzing conditions. The case in which the reaggregating button 3980 is selected after the analyzing condition is changed corresponds to the case in which the aggregating condition is changed.

Figure 40:
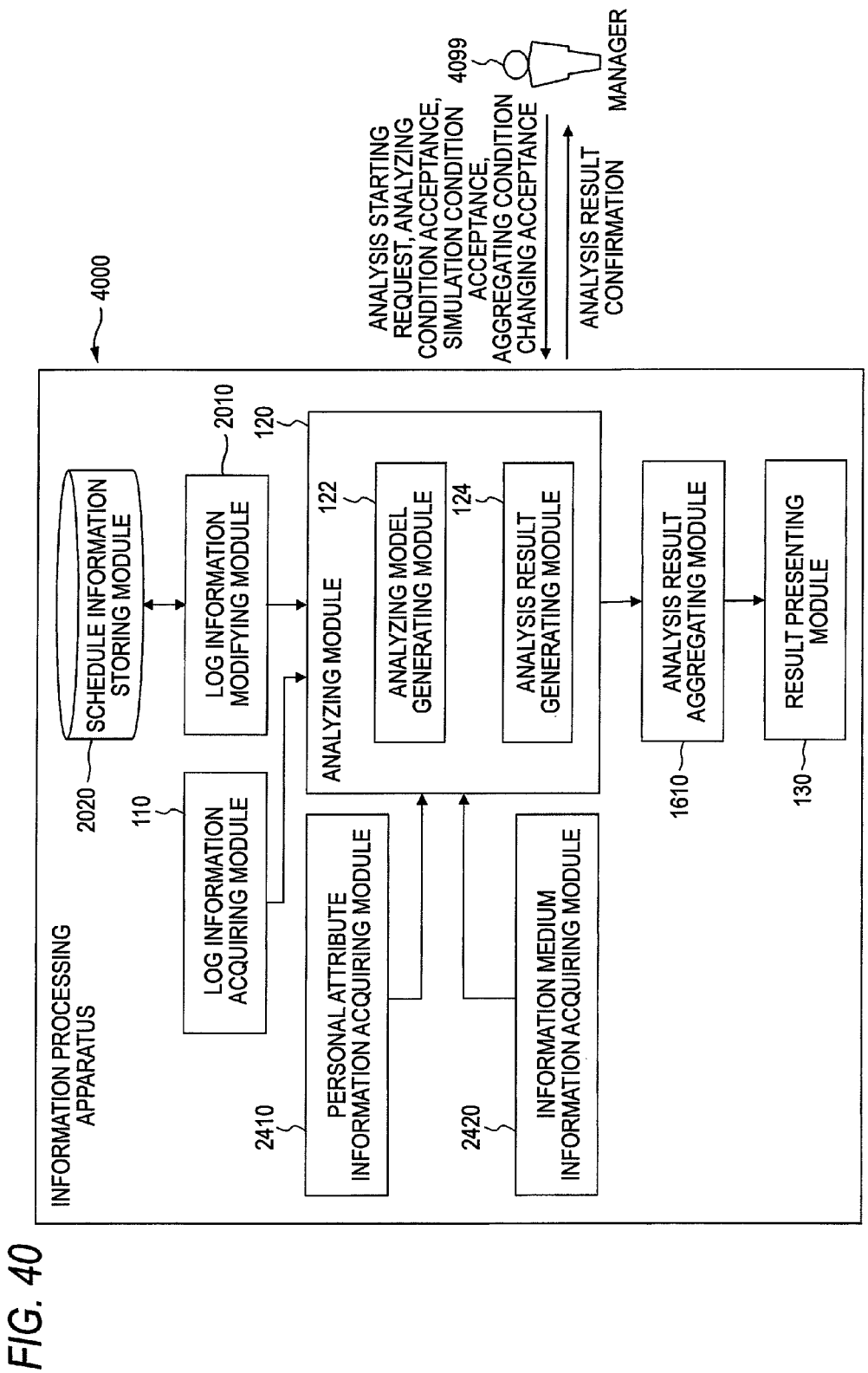
FIG. 40 is a diagram showing a conceptual module structure according to an example of a structure in accordance with a (2-C)th exemplary embodiment.

FIG. 40 is a diagram showing a conceptual module structure according to an example of a structure in accordance with the (2-C)th exemplary embodiment. An information processing apparatus 4000 has a log information acquiring module 110, a log information modifying module 2010, a schedule information storing module 2020, an analyzing module 120, a personal attribute information acquiring module 2410, an information medium information acquiring module 2420, an analysis result aggregating module 1610, and a result presenting module 130.

In the (2-C)th exemplary embodiment, past action log data or log data of an image output device are changed to carry out a simulation or schedule information to be a future schedule (for example, an entrance of a user into an area in which the image output device is installed or a print of a material to be utilized in a conference by the user) is used to carry out a simulation.

The log information modifying module 2010 is connected to the analyzing module 120 and the schedule information storing module 2020. The log information modifying module 2010 serves to modify one of action log data on an event including at least a starting date and time of an event, an ending date and time of the event, and a place for an occurrence of the event which are stored in an indoor action log DB 2312 or an apparatus operating log DB 2314, or their combination. Moreover, it is also possible to carry out a modification for adding schedule information about a target user or the image output device through the schedule information storing module 2020 for storing schedule information about an event including at least a starting date and time of an event, an ending date and time of the event and a place for an occurrence of the event which are future schedules of the user or the image output device. The modification includes a change and deletion of the log data stored in the indoor action log DB 2312 or the apparatus operating log DB 2314, and furthermore, a new addition of information generated from the schedule information as log data.

The schedule information storing module 2020 is connected to the log information modifying module 2010. The schedule information storing module 2020 stores information including at least the starting date and time of the event, the ending date and time of the event and the place for the occurrence of the event which are the schedule information, that is, the future schedules of the user or the image output device. Moreover, the schedule DB 520 and the schedule information managing server host 515 which are illustrated in FIG. 5 may be added to the example of the system structure shown in FIG. 23 to store the schedule information in the schedule DB 520. The information in the schedule information storing module 2020 is acquired from the schedule DB 520.

Figure 41:
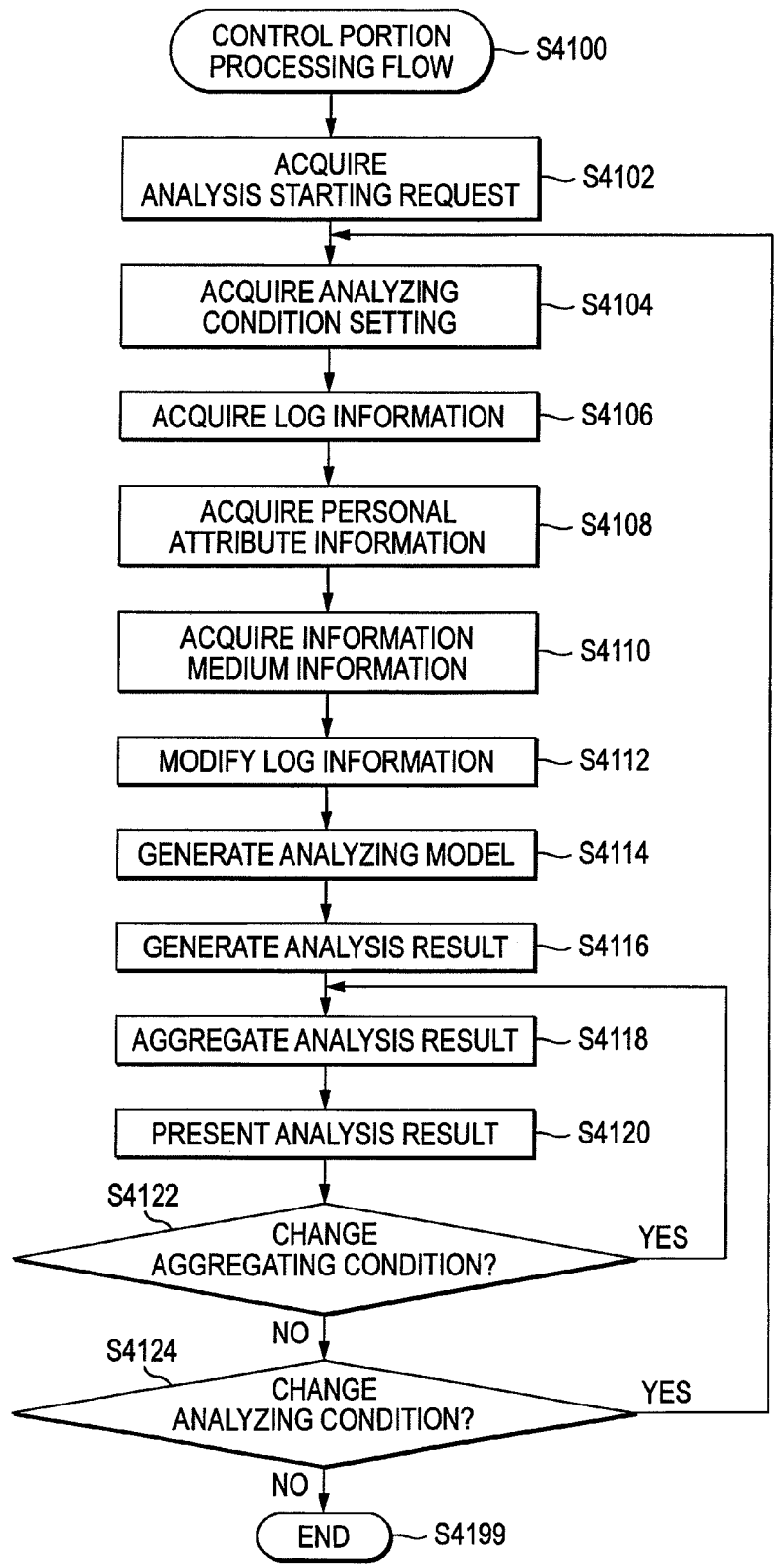
FIG. 41 is a flowchart showing an example of a processing according to the (2-C)th exemplary embodiment.

FIG. 41 is a flowchart showing an example of a processing according to the (2-C)th exemplary embodiment. In the case of the same processing as that in the flowchart showing the example of the processing according to the (2-B)th exemplary embodiment illustrated in FIG. 37, the steps illustrated in the example of FIG. 37 will be shown and description will be omitted.

At Step S4102, the information processing apparatus 4000 acquires an analysis starting request. An equivalent processing to the Step S3702 is executed.

At Step S4104, the information processing apparatus 4000 acquires analyzing condition setting. An equivalent processing to the Step S3704 is executed.

At Step S4106, the log information acquiring module 110 acquires log information. An equivalent processing to the Step S3706 is executed.

At Step S4108, the personal attribute information acquiring module 2410 acquires personal attribute information. An equivalent processing to the Step S3708 is executed.

At Step S4110, the information medium information acquiring module 2420 acquires information medium information. An equivalent processing to the Step S3710 is executed.

Figure 42:
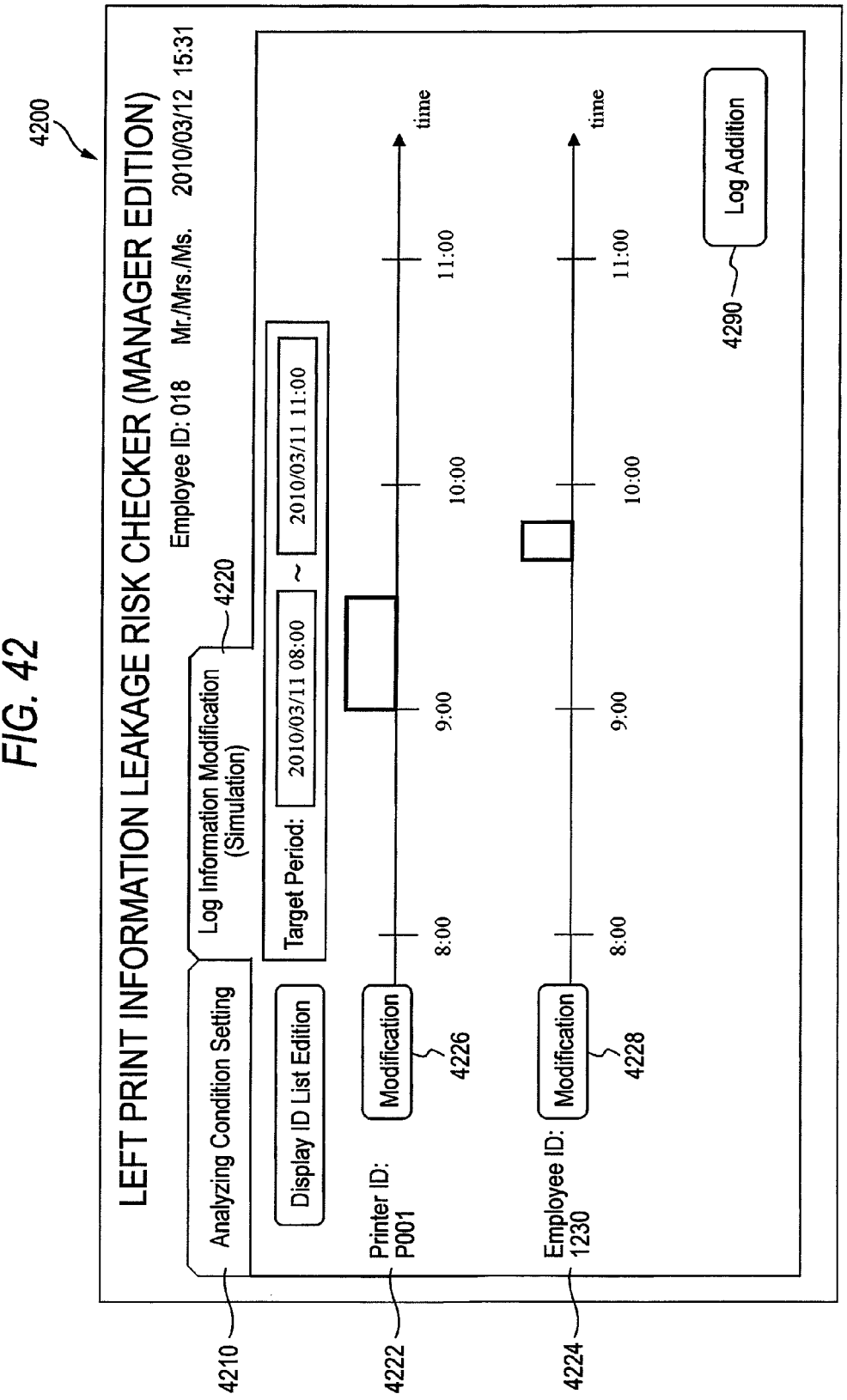
FIG. 42 is an explanatory diagram showing an example of a left print information leakage risk simulation screen.

At Step S4112, the log information modifying module 2010 modifies log information. By operating a mouse, a keyboard or a touch panel through a manager 4099, a simulation condition is accepted and the log data in the indoor action log DB 2312 or the apparatus operating log DB 2314 are modified. For example, a screen for setting the simulation condition includes a left print information leakage risk simulation screen 4200. FIG. 42 is an explanatory diagram showing an example of the left print information leakage risk simulation screen 4200. The left print information leakage risk simulation screen 4200 has an analyzing condition setting tab 4210 and a log information modifying (simulation) tab 4220. The log information modifying (simulation) tab 4220 has a target printer (P001) log display region 4222 and a target employee (1230) log display region 4224 which serve to present past log data of a target image output device or user, a modifying button 4226 and a modifying button 4228 which serve to modify the log data, and a log adding button 4290 for newly adding action log data from schedule information. Although a date and time that a user enters a room, a date and time that the user leaves the room, and a leaving starting date and time and a leaving ending date and time of an image output device may be varied in the example of FIG. 42, it is also possible to additionally change the room or the image output device. In the case in which the log adding button 4290 is selected, moreover, the log information modifying module 2010 fetches schedule information about a target user or image output device from the schedule information storing module 2020 and adds the schedule information as the log data.

At Step S4114, an analyzing model generating module 122 generates an analyzing model. An equivalent processing to the Step S3712 is executed.

At Step S4116, an analysis result generating module 124 generates an analysis result. An equivalent processing to the Step S3714 is executed.

At Step S4118, the analysis result aggregating module 1610 aggregates the analysis result. An equivalent result to the Step S3716 is executed.

At Step S4120, the result presenting module 130 presents the analysis result. An equivalent processing to the Step S3718 is executed.

At Step S4122, the analysis result aggregating module 1610 decides whether an aggregating condition is changed or not. If the aggregating condition is changed, the processings in and after the Step S4118 are executed. In the other cases, the processing proceeds to Step S4124. An equivalent processing to the Step S3720 is executed.

At the Step S4124, the log information modifying module 2010 decides whether an analyzing condition is changed or not. If the analyzing condition is changed, the processings in and after the Step S4104 are executed. In the other cases, the processing is ended (Step S4199).

Although the analysis result aggregating module 1610 is used as is illustrated in FIG. 40 in the (2-C)th exemplary embodiment, it is also possible to eliminate the analysis result aggregating module 1610 and to connect the analyzing module 120 to the result presenting module 130. A general user may make use in place of the manager 4099 as in the (2-A)th exemplary embodiment.

Although the printer or the composite machine is shown as an example of the image output device in the second exemplary embodiment (including the (2-A)th exemplary embodiment, the (2-B)th exemplary embodiment and the (2-C)th exemplary embodiment), moreover, a copying machine or a fax may be employed.

By using, as the operating log of the image output device, a log constituted by times that an electronic document is opened and closed over a display device of an information processing apparatus such as a PC which may be operated by a user, a place in which the information processing apparatus is installed, and a document ID thereof, position information about a person, information medium information, and personal attribute information, furthermore, it is also possible to analyze the information leakage risk by stealing a glance at the display device in the same manner as the left print.

Figure 43:
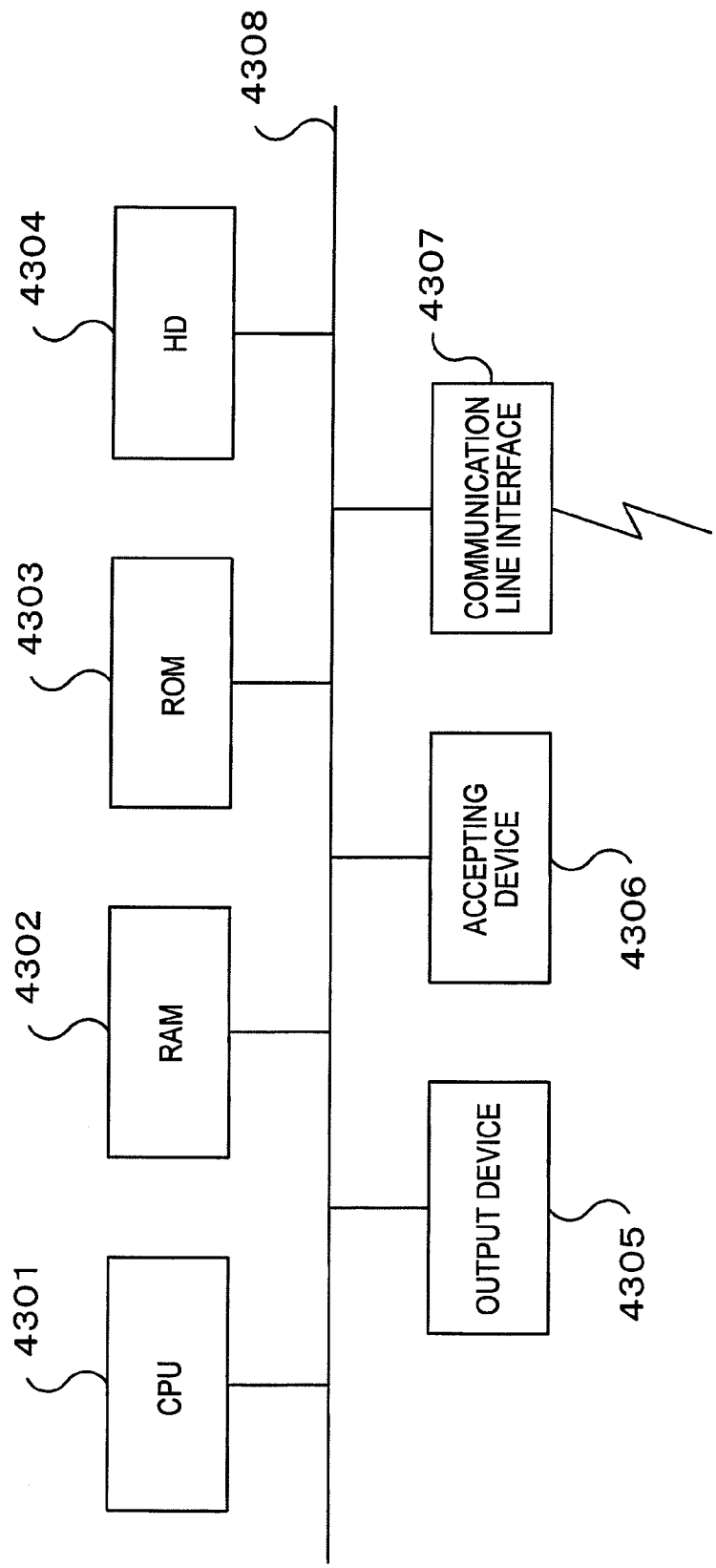
FIG. 43 is a block diagram showing an example of a hardware structure of a computer for implementing the (1-A)th exemplary embodiment to (2-C)th exemplary embodiment.

A hardware structure of a computer to execute a program according to the exemplary embodiment is a general computer as is illustrated in FIG. 43, specifically, a personal computer or a computer capable of being used as a server. In other words, as a specific example, a CPU 4301 is used as a processing portion (a calculating portion), and an RAM 4302, an ROM 4303 and an HD 4304 are used as storage devices. As the HD 4304, a hard disk may be used, for example. The computer is constituted by the CPU 4301 for executing a program of the log information acquiring module 110, the analyzing model generating module 122, the analysis result generating module 124, the result presenting module 130, the analysis result aggregating module 1610, the log information modifying module 2010, the personal attribute information acquiring module 2410 or the information medium information acquiring module 2420, the RAM 4302 for storing the program or data, the ROM 4303 storing a program for activating the computer, the HD 4304 to be an auxiliary storage device, an accepting device 4306 for accepting data based on an operation of a user for a keyboard, a mouse or a touch panel, an output device 4305 such as a CRT or a liquid crystal display, a communication line interface 4307 for carrying out a connection to a communication network such as a network interface card, and a bus 4308 for connecting them to transfer/receive data. A plurality of computers may be connected through a network.

Referring to the computer program according to any of the exemplary embodiments, a system of the hardware structure is caused to read the computer program to be software, and the software and hardware resources are cooperated with each other so that the exemplary embodiment is implemented.

The hardware structure shown in FIG. 43 indicates one of the examples of the structures. It is sufficient that the exemplary embodiments may employ a structure capable of executing the modules according to the exemplary embodiments in addition to the structure shown in FIG. 43. For example, a part of the modules may be constituted by dedicated hardware (for example, ASIC) or may be provided in an external system and connected through a communication line. In addition, the systems shown in FIG. 43 may be connected to each other through a communication line and thus carry out a cooperating work each other. In particular, they may be incorporated in information household appliances, a copying machine, a fax, a scanner, a printer or a composite machine in addition to a personal computer.

The program may be stored in a recording medium and be thus offered. Moreover, the program may be offered through communicating means. In that case, for example, the program may be grasped as the invention of a "computer readable recording medium recording a program".

The "computer readable recording medium recording a program" represents a computer readable recording medium recording a program which is used for a program installation, an execution or a program distribution.

For example, the recording medium includes a digital versatile disc (DVD) such as "DVD-R, DVD-RW or DVD-RAM" on a standard developed in a DVD forum or "DVD+R or DVD+RW" on a standard developed in DVD+RW, a compact disc (CD) such as a read only memory (CD-ROM), CD recordable (CD-R) or CD rewritable (CD-RW), Blue-ray Disc (registered trademark), a magneto-optical disk (MO), a flexible disk (FD), a magnetic tape, a hard disk, a read only memory (ROM), an electrically erasable/programmable read only memory (EEPROM), a flash memory, and a random access memory (RAM).

The programs or a part of them may be recorded in the recording medium, and may be thus stored or distributed. Moreover, they may be transmitted through a communication, for example, a transmitting medium such as a cable network to be used for a local area network (LAN), a metropolitan area network (MAN), a wide area network (WAN), internet, intranet Or extranet, a radio communication network, or their combination, or may be delivered over a carrier wave.

Furthermore, the programs may be a part of the other programs or may be recorded in a recording medium together with separate programs. Moreover, they may be divided and recorded in a plurality of recording media. In addition, they may be recorded in any manner if a reconstruction such as a compression or an encryption may be carried out.

The foregoing description of the exemplary embodiment of the present invention has been provided for the purpose of illustration and description. It is not intended to be exhaustive or to limit the invention to the precise forms disclosed. Obviously, many modifications and various will be apparent to practitioners skilled in the art. The embodiments were chosen and described in order to best explain the principles of the invention and its practical application, thereby enabling other skilled in the art to understand the invention for various embodiments and with the various modifications as are suited to the particular use contemplated. It is intended that the scope of the invention be defined by the following claims and their equivalents.

DESCRIPTION OF THE REFERENCE NUMERALS AND SIGNS

100 information processing apparatus
110 log information acquiring module
120 analyzing module
122 analyzing model generating module
124 analysis result generating module
130 result presenting module
505 log DB server host
510 indoor action log DB
515 schedule information managing server host
520 schedule DB
525 position information server host
530 position sensor
535 analyzing server host
540 area characteristic DB
545 personal attribute information DB
550 infection risk DB
555 infection state DB
560 analyzing client host
585 tag
599 communication line
1600 information processing apparatus
1610 analysis result aggregating module
2000 information processing apparatus
2010 log information modifying module
2020 schedule information storing module
2310 log DB server host
2312 indoor action log DB
2314 apparatus operating log DB
2320 analyzing server host
2322 personal attribute information DB
2324 area characteristic DB
2326 information medium information DB
2328 printer information DB
2330 position information server host
2335 position sensor
2340 apparatus operating information server host
2342 PC
2344 composite machine
2350 analyzing client host
2385 tag
2399 communication line
2400 information processing apparatus
2410 personal attribute information acquiring module
2420 information medium information acquiring module

What is claimed is:
1. An information processing apparatus comprising:
an acquiring module, as executed by the information processing apparatus, that acquires information corre- sponding to a first event including a starting point of the first event, an ending point of the first event, and a location of the first event, and acquires information corresponding to a second event including a starting point of the second event, an ending point of the second event, and a location of the second event, the location of the second event and the location of the first event being a same location;

a model generating module that generates a first model of the first event and a second model of the second event, the first model including:
  an ending point that is a predetermined time after the ending point of the first event; and
  influence information for calculating an influence of the first event,
the second model including:
  a starting point that corresponds to the starting point of the second event; and
  influence information for calculating an influence of the second event, the influence information for calculating an influence of the second event being used to calculate the starting point of the second model; and
an analyzing module that analyzes an influence of a combination of the first event and the second event based on:
  an overlap period corresponding to the starting point of the second model and the ending point of the first model; and
  at least one of the influence information of the first model and the influence information of the second model,
wherein the ending point of the first event is before the starting point of the second event, and
wherein the starting point of the second model is a predetermined amount of time before the starting point of the second event.

2. The information processing apparatus according to claim 1, further comprising an output module that outputs an analysis result obtained by the analyzing module.

3. The information processing apparatus according to claim 1, further comprising a totalizing module that totalizes the analysis result obtained by the analyzing module based on an operating instruction of a user.

4. The information processing apparatus according to claim 1, further comprising:
  an event information storage device that stores the information of the first event and the information of the second event; and
  a modifying module that modifies, for at least one of the information of the first event and the information of the second event, one or more of the respective starting point, ending point, and location which are stored in the event information storage device,
wherein the model generating module generates the first model and the second model so as to correspond with information having been modified by the modifying module.

5. The information processing apparatus according to claim 4, wherein the modifying module modifies information of a future event by adding schedule information about a corresponding user through a schedule information storing module that stores schedule information corresponding to a future schedule of the corresponding user, the schedule information including a starting point of the future event, an ending point of the future event, and a location of the future event.

6. The information processing apparatus according to claim 1, wherein the starting point of the second model is before the ending point of the first model.

7. The information processing apparatus according to claim 1, wherein the second model further includes a ending point that is after the ending point of the second event.

8. An information processing method comprising:
  acquiring, as executed by an information processing apparatus, information corresponding to a first event including a starting point of the first event, an ending point of the first event, and a location of the first event;
  acquiring information corresponding to a second event including a starting point of the second event, an ending point of the second event, and a location of the second event, the location of the second event and the location of the first event being a same location;
  generating a first model of the first event, the first model including:
    an ending point that is a predetermined time after the ending point of the first event; and
    influence information for calculating an influence of the first event;
  generating a second model of the second event, the second model including:
    a starting point that corresponds to the starting point of the second event; and
    influence information for calculating an influence of the second event, the influence information for calculating an influence of the second event being used to calculate the starting point of the second model; and
  analyzing an influence of a combination of the first event and the second event based on:
    an overlap period corresponding to the starting point of the second model and the ending point of the first model; and
    at least one of the influence information of the first model and the influence information of the second model,
  wherein the starting point of the second model is a predetermined amount of time before the starting point of the second event.

9. The information processing method according to claim 8, wherein the starting point of the second model is before the ending point of the first model.

10. A non-transitory computer readable medium storing a program for causing a computer to execute a process for information processing, the process for information processing comprising:
  acquiring information corresponding to a first event including a starting point of the first event, an ending point of the first event, and a location of the first event;
  acquiring information corresponding to a second event including a starting point of the second event, an ending point of the second event, and a location of the second event, the location of the second event and the location of the first event being a same location;
  generating a first model of the first event, the first model including:
    an ending point that is a predetermined time after the ending point of the first event; and
    influence information for calculating an influence of the first event;
  generating a second model of the second event, the second model including:
    a starting point that corresponds to the starting point of the second event; and influence information for calculating an influence of the second event, the influence information for calculating an influence of the second event being used to calculate the starting point of the second model; and analyzing an influence of a combination of the first event and the second event based on:
- an overlap period corresponding to the starting point of the second model and the ending point of the first model; and
- at least one of the influence information of the first model and the influence information of the second model, wherein the ending point of the first event is before the starting point of the second event, and wherein the starting point of the second model is a predetermined amount of time before the starting point of the second event.

11. The non-transitory computer readable medium according to claim 10, wherein the starting point of the second model is before the ending point of the first model.

12. A system comprising:

a model generating module, as executed by a processor, that generates a first model of a first event and a second model of a second event, the first event having a period that does not overlap a period of the second event, the first model modeling an influence of the first event and the second model modeling an influence of the second event, the first model having a period that overlaps a period of the second model; and an analyzing module that analyzes an influence between the first event and the second based on the first model, the second model, and a period of the overlap between the period of the first model and the period of the second model, wherein the starting point of the second model is a predetermined amount of time before the starting point of the second event.

\* \* \* \* \*